(12) United States Patent
Hinoishi et al.

(10) Patent No.: US 10,370,309 B2
(45) Date of Patent: Aug. 6, 2019

(54) METHOD FOR PRODUCING CONJUGATED DIENE

(71) Applicant: Mitsubishi Chemical Corporation, Chiyoda-ku (JP)

(72) Inventors: Hiroki Hinoishi, Okayama (JP); Kazuyuki Iwakai, Okayama (JP); Hiroshi Kameo, Okayama (JP)

(73) Assignee: Mitsubishi Chemical Corporation, Chiyoda-ku (KR)

( * ) Notice: Subject to any disclaimer, the term of this patent is extended or adjusted under 35 U.S.C. 154(b) by 0 days.

(21) Appl. No.: 15/699,666

(22) Filed: Sep. 8, 2017

(65) Prior Publication Data

US 2017/0369400 A1    Dec. 28, 2017

Related U.S. Application Data

(63) Continuation of application No. PCT/JP2016/057162, filed on Mar. 8, 2016.

(30) Foreign Application Priority Data

Mar. 9, 2015  (JP) ................................. 2015-046057
Mar. 19, 2015  (JP) ................................. 2015-056589

(51) Int. Cl.
*C07C 5/48*       (2006.01)
*C07C 7/09*       (2006.01)
(Continued)

(52) U.S. Cl.
CPC .............. *C07C 5/48* (2013.01); *B01J 23/002* (2013.01); *B01J 23/8876* (2013.01); *C07C 7/09* (2013.01);
(Continued)

(58) Field of Classification Search
CPC ... C07C 5/48; C07C 2523/887; C07C 11/167; B01J 23/002; B01J 23/8876; B01J 2523/00
See application file for complete search history.

(56) References Cited

U.S. PATENT DOCUMENTS

2012/0130137 A1   5/2012  Orita et al.
2014/0114108 A1   4/2014  Yano et al.

FOREIGN PATENT DOCUMENTS

EP    0 872 472 A1    10/1998
JP    57-31637 A       2/1982
(Continued)

OTHER PUBLICATIONS

Extended European Search Report dated Feb. 20, 2018 in Patent Application No. 16761751.3, 9 pages.
(Continued)

*Primary Examiner* — Brian A McCaig
*Assistant Examiner* — Jason Y Chong
(74) *Attorney, Agent, or Firm* — Oblon, McClelland, Maier & Neustadt, L.L.P.

(57) ABSTRACT

The invention is concerned with a method for producing a conjugated diene including a reaction step of subjecting a raw material gas containing a monoolefin having a carbon atom number of 4 or more to an oxidative dehydrogenation reaction with a gas containing molecular oxygen in the presence of a catalyst, to obtain a reaction product gas containing a conjugated diene; and a cooling step of cooling the reaction product gas, wherein in the cooling step, a cooling agent is supplied into a cooling column and brought into contact with the reaction product gas; the cooling agent discharged from the cooling column is then cooled by a heat exchanger; a precipitate dissolved in the cooling agent is precipitated within the heat exchanger and recovered; and
(Continued)

the cooling agent from which the precipitate has been recovered is circulated into the cooling column.

14 Claims, 7 Drawing Sheets

(51) Int. Cl.
*C07C 7/11* (2006.01)
*C07C 11/167* (2006.01)
*B01J 23/00* (2006.01)
*B01J 23/887* (2006.01)
*C07B 61/00* (2006.01)

(52) U.S. Cl.
CPC .............. *C07C 7/11* (2013.01); *C07C 11/167* (2013.01); *B01J 2523/00* (2013.01); *C07B 61/00* (2013.01); *C07C 2523/887* (2013.01); *Y02P 20/51* (2015.11); *Y02P 30/464* (2015.11)

(56) References Cited

FOREIGN PATENT DOCUMENTS

| | | |
|---|---|---|
| JP | 60-115531 A | 6/1985 |
| JP | 61-5030 A | 1/1986 |
| JP | 11-1454 A | 1/1999 |
| JP | 2011-1341 A | 1/2011 |
| JP | 2011-6381 A | 1/2011 |
| JP | 2011-132218 A | 7/2011 |
| JP | 2012-67048 A | 4/2012 |
| JP | 2013-119530 A | 6/2013 |
| JP | 2013-177380 A | 9/2013 |
| JP | 2013-213028 A | 10/2013 |
| JP | 2014-198707 A | 10/2014 |
| SU | 1417409 A1 | 12/1999 |
| WO | WO 2012/157495 A1 | 11/2012 |
| WO | WO 2014/086813 A1 | 6/2014 |
| WO | WO 2014/111406 A1 | 7/2014 |
| WO | WO 2015/007841 A1 | 1/2015 |

OTHER PUBLICATIONS

International Search Report dated May 31, 2016 in PCT/JP2016/057162 (with English translation).
Written Opinion of the Search Authority dated May 31, 2016 in PCT/JP2016/057162.
Office Action issued May 7, 2019, in Russian Patent Application No. 20170131411, filed Mar. 8, 2016 (with English Translation).

METHOD FOR PRODUCING CONJUGATED DIENE

CROSS-REFERENCES TO RELATED APPLICATIONS

This application is a Continuation of PCT/JP2016/057162, which was filed on Mar. 8, 2016. This application is based upon and claims the benefit of priority to Japanese Application No. 2015-046047, which was file don Mar. 9, 2015, and to Japanese Application No. 2015-056589, which was filed on Mar. 19, 2015.

TECHNICAL FIELD

The present invention relates to a method for producing a conjugated diene, and in particular, the invention relates to a method for producing a conjugated diene, such as butadiene, etc., through a catalytic oxidative dehydrogenation reaction of a monoolefin having a carbon atom number of 4 or more, such as n-butene, etc.

BACKGROUND ART

A method for producing a conjugated diene, such as butadiene, etc., through a catalytic oxidative dehydrogenation reaction of a monoolefin, such as n-butene, etc., has hitherto been known. In addition, various investigations regarding the separation of a high boiling point by-product in a formed gas have also been made.

For example, Patent Document 1 discloses an invention in which a minute amount of a high boiling point by-product contained in a product gas is introduced into a quench column (cooling column) in which a wall surface temperature within the column is kept at a specified temperature and brought into contact with spray water to separate the high boiling point by-product.

Patent Document 2 discloses a method in which a reaction product gas is introduced into a quench column (cooling column), and an alkaline substance is poured into cold water to be supplied into the column top of the quench column, thereby dissolving a high boiling point by-product composed mainly of an organic acid in an aqueous phase to remove it.

Patent Document 3 discloses a method in which a reaction product gas is introduced into a quench column (cooling column), and a sublimable high boiling point reaction by-product is removed by using, as a quenching agent (cooling agent), an organic amine aqueous solution or an aromatic organic solvent.

Patent Document 4 discloses a production method of using a circulating liquid containing an alkaline compound by using a quench column in which a cooling step of a reaction product gas has two or more zones. Patent Document 5 discloses a method in which a reaction product gas is preliminarily cooled and then supplied into a quench column (cooling column). Patent Document 6 discloses a method in which a column bottom liquid of a cooling column is subjected to swirling fluidization along a wall surface of the cooling column.

CITATION LIST

Patent Document

Patent Document 1: JP-A-S60-115531
Patent Document 2: JP-A-S61-5030
Patent Document 3: WO-2012/157495
Patent Document 4: JP-A-2012-67048
Patent Document 5: JP-A-2011-1341
Patent Document 6: JP-A-2014-198707

SUMMARY OF INVENTION

Technical Problem

However, even if the high boiling point by-product is dissolved in a cooling agent, such as an alkaline aqueous solution, an organic solvent, etc., and removed from a reaction gas, when the cooling agent is circulated, the high boiling point by-product is also circulated into the cooling column, and as a result, is accumulated within the cooling column to generate fouling, thereby causing clogging.

In consequence, a problem of the present invention is to provide a method for producing a conjugated diene through an oxidative dehydrogenation reaction of a monoolefin having a carbon atom number of 4 or more, in which a high boiling point by-product, especially 9-fluorenone or the like, which has high crystallinity so that clogging of a piping or the like is highly possibly caused, is removed from a reaction gas in a cooling column and further removed from a cooling agent, thereby more stably producing a conjugated diene, such as butadiene, etc., without resulting in clogging the piping or equipment to be caused due to precipitation of the high boiling point by-product.

Solution to Problem

In order to solve the foregoing problem, the present inventors made extensive and intensive investigations regarding a high boiling point by-product contained in a reaction gas. As a result, it has been found that the removal of the high boiling point by-product can be achieved by a cooling column with water as a circulating liquid, which has hitherto been considered to be impossible.

Furthermore, it has been found that in a method for producing a conjugated diene, such as butadiene, etc., through a catalytic oxidative dehydrogenation reaction of a monoolefin, such as n-butene, etc., when a reaction product gas is introduced into the cooling column with water as a cooling agent and achieving cooling, by operating the cooling column of the reaction gas under a specified operation condition, and especially specifying a cooling condition of the cooling agent, it is possible to remove the high boiling point by-product, and as a result, the conjugated diene, such as butadiene, etc., can be more stably produced without resulting in clogging the piping or equipment to be caused due to precipitation of the high boiling point by-product.

Namely, the present invention relates to the following [1] to [18].

[1] A method for producing a conjugated diene including a reaction step of subjecting a raw material gas containing a monoolefin having a carbon atom number of 4 or more to an oxidative dehydrogenation reaction with a gas containing molecular oxygen in the presence of a catalyst, to obtain a reaction product gas containing a conjugated diene; and a cooling step of cooling the reaction product gas, wherein.

in the cooling step, a cooling agent is supplied into a cooling column and brought into contact with the reaction product gas; the cooling agent discharged from the cooling column is then cooled by a heat exchanger; a precipitate dissolved in the cooling agent is precipitated within the heat exchanger and recovered; and the cooling agent from which the precipitate has been recovered is circulated into the cooling column.

[2] The method for producing a conjugated diene according to the above [1], wherein the cooling agent is water.

[3] The method for producing a conjugated diene according to the above [1] or [2], wherein the precipitate is 9-fluorenone.

[4] The method for producing a conjugated diene according to any one of the above [1] to [3], wherein two or more of the heat exchangers are provided.

[5] The method for producing a conjugated diene according to the above [4], wherein the heat exchangers are arranged in at least either a parallel direction or a series direction.

[6] The method for producing a conjugated diene according to any one of the above [1] to [5], wherein a liquid linear rate in the heat exchanger for precipitating the precipitate is 1.0 m/sec or less.

[7] The method for producing a conjugated diene according to any one of the above [3] to [6], wherein a concentration of 9-fluorenone in the cooling agent to be circulated into the cooling column is 30 ppm by weight or less.

[8] The method for producing a conjugated diene according to any one of the above [1] to [7], wherein the raw material gas is a gas containing 1-butene, cis-2-butene, or tans-2-butene, each of which is obtained by dimerization of ethylene, or a mixture thereof; a butene fraction which is produced through a dehydrogenation or oxidative dehydrogenation reaction of n-butane; or a gas containing a hydrocarbon having a carbon atom number of 4, which is obtained on performing fluid catalytic cracking of a fuel oil fraction.

[9] A method for producing a conjugated diene including a reaction step of subjecting a raw material gas containing a monoolefin having a carbon atom number of 4 or more to an oxidative dehydrogenation reaction with a gas containing molecular oxygen in the presence of a catalyst, to obtain a reaction product gas containing a conjugated diene; and a cooling step of cooling the reaction product gas, wherein.

in the cooling step, a cooling agent is supplied into a cooling column and brought into contact with the reaction product gas; the cooling agent discharged from the cooling column is then cooled by a condenser; a precipitate precipitated by cooling is recovered by a separation apparatus; and the cooling agent from which the precipitate has been recovered is circulated into the cooling column.

[10] The method for producing a conjugated diene according to the above [9], wherein the cooling agent is water.

[11] The method for producing a conjugated diene according to the above [9] or [10], wherein the precipitate is 9-fluorenone.

[12] The method for producing a conjugated diene according to any one of the above [9] to [11], wherein two or more of the separation apparatus are provided.

[13] The method for producing a conjugated diene according to any one of the above [9] to [12], wherein the condenser is a heat exchanger, and a liquid linear rate in the condenser is faster than 1.0 m/sec.

[14] The method for producing a conjugated diene according to any one of the above [11] to [13], wherein a concentration of 9-fluorenone in the cooling agent to be circulated into the cooling column is 30 ppm by weight or less.

[15] The method for producing a conjugated diene according to any one of the above [9] to [14], wherein the raw material gas is a gas containing 1-butene, cis-2-butene, or tans-2-butene, each of which is obtained by dimerization of ethylene, or a mixture thereof; a butene fraction which is produced through a dehydrogenation or oxidative dehydrogenation reaction of n-butane; or a gas containing a hydrocarbon having a carbon atom number of 4, which is obtained on performing fluid catalytic cracking of a fuel oil fraction.

[16] A method for producing a conjugated diene including a reaction step of subjecting a raw material gas containing a monoolefin having a carbon atom number of 4 or more to an oxidative dehydrogenation reaction with a gas containing molecular oxygen in the presence of a catalyst, to obtain a reaction product gas containing a conjugated diene; and a cooling step of cooling the reaction product gas, wherein.

in the cooling step, water is used as a cooling agent; and when the cooling agent is supplied into a cooling column and brought into contact with the reaction product gas, and the cooling agent discharged from the cooling column is then cooled by a heat exchanger and circulated into the cooling column, by regulating a liquid linear rate of the cooling agent passing through the heat exchanger to 1.0 m/sec or less, 9-fluorenone is accumulated within the heat exchanger; and the 9-fluorenone is separated from the cooling agent, or by making a liquid linear rate of the cooling agent passing through the heat exchanger faster than 1.0 m/sec to pass through the heat exchanger, 9-fluorenone is then separated from the cooling agent by a separation apparatus.

[17] The method for producing a conjugated diene according to the above [16], wherein a concentration of 9-fluorenone in the cooling agent to be circulated into the cooling column is 30 ppm by weight or less.

[18] The method for producing a conjugated diene according to the above [16] or [17], wherein the raw material gas is a gas containing 1-butene, cis-2-butene, or tans-2-butene, each of which is obtained by dimerization of ethylene, or a mixture thereof; a butene fraction which is produced through a dehydrogenation or oxidative dehydrogenation reaction of n-butane; or a gas containing a hydrocarbon having a carbon atom number of 4, which is obtained by performing fluid catalytic cracking of a fuel oil fraction.

Effect of the Invention

In accordance with the present invention, in producing a conjugated diene through an oxidative dehydrogenation reaction of a monoolefin having a carbon atom number of 4 or more, it becomes possible to more stably produce a conjugated diene, such as butadiene, etc., without resulting in clogging the piping or equipment to be caused due to precipitation of a high boiling point by-product.

DESCRIPTION OF EMBODIMENTS

Figure 1:
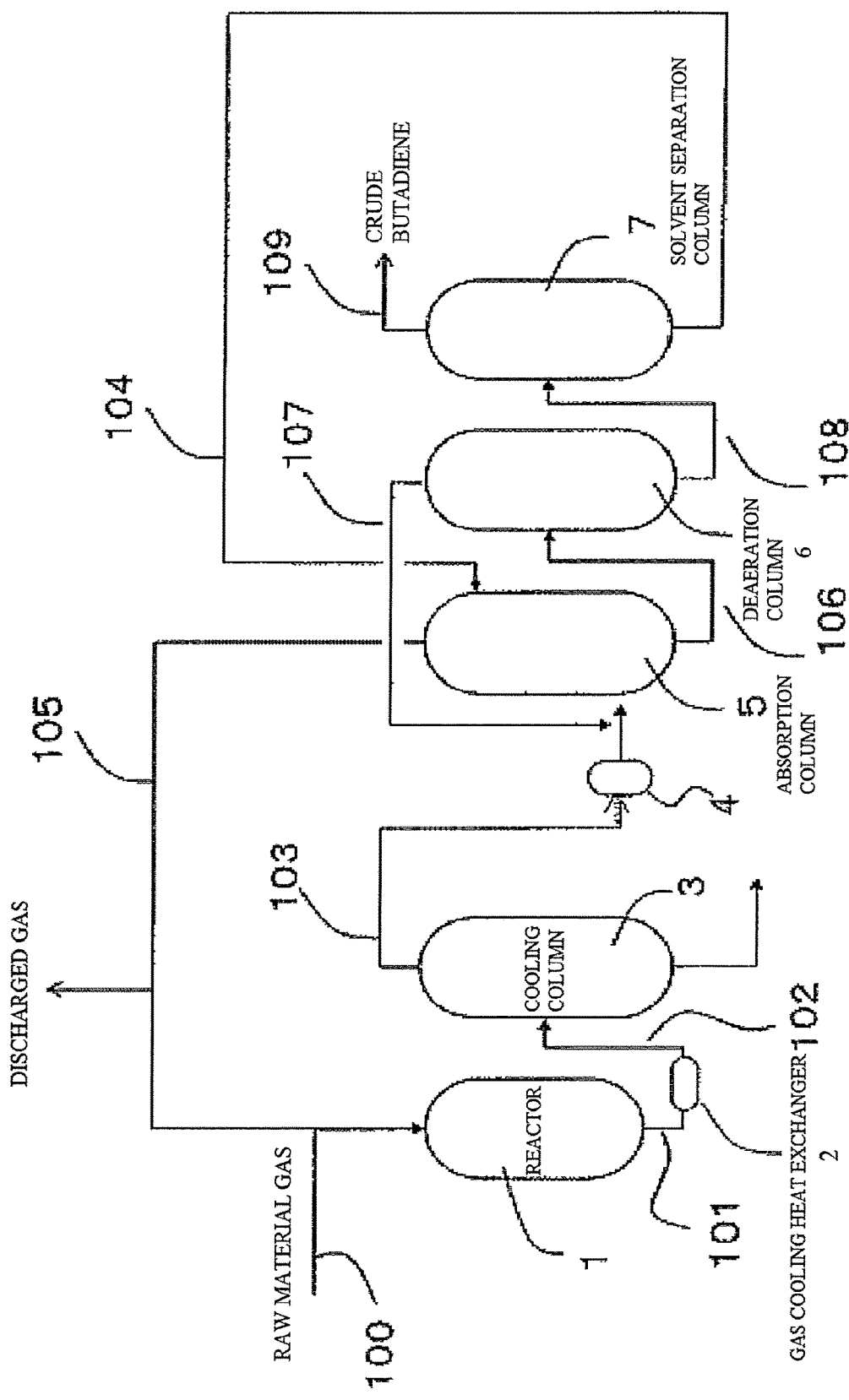
FIG. 1 is a process diagram showing a mode for carrying out a method for producing a conjugated diene according to the present invention.

Modes for carrying out a method for producing a conjugated diene according to the present invention are hereunder described in detail. However, the following description is concerned with one example (representative example) of embodiments according to the present invention, and the present invention is not limited to the contents thereof.

1. Reaction Step:

In the present invention, a raw material gas containing a monoolefin having a carbon atom number of 4 or more and a gas containing molecular oxygen are supplied into a reactor having a catalyst layer, and a corresponding conjugated diene is produced through an oxidative dehydrogenation reaction.

<Raw Material Gas Containing Monoolefin Having a Carbon Atom Number of 4 or More>

The raw material gas for use in the present invention contains a monoolefin having a carbon atom number of 4 or more. Examples of the monoolefin having a carbon atom number of 4 or more include monoolefins having a carbon atom number of 4 or more, and preferably a carbon atom number of 4 to 6, such as butenes (for example, n-butene, such as 1-butene, 2-butene, etc., and isobutene), pentene, methylbutene, dimethylbutene, etc. Such a monoolefin can be effectively applied for the production of a corresponding conjugated diene through a catalytic oxidative dehydrogenation reaction. Of these, such a monoolefin is most suitably used for the production of butadiene from n-butene (for example, n-butene, such as 1-butene, 2-butene, etc.).

In addition, as the raw material gas containing a monoolefin having a carbon atom number of 4 or more, an isolated monoolefin per se having a carbon atom number of 4 or more is not necessarily used, and the monoolefin can be in a form of an arbitrary mixture, if desired.

For example, in the case where it is intended to obtain butadiene, although high-purity n-butene (at least either 1-butene or 2-butene) can be used as the raw material gas, a fraction (BBSS) containing, as a main component, n-butene (at least either 1-butene or 2-butene) obtained by separating butadiene and i-butene from a C4 fraction (BB) which is formed as a by-product in naphtha cracking, or a butene fraction which is produced through a dehydrogenation or oxidative dehydrogenation reaction of n-butane can also be used.

In addition, a gas containing high-purity 1-butene, cis-2-butene, or tans-2-butene, each of which is obtained by dimerization of ethylene, or a mixture thereof, may also be used as the raw material gas.

As for this ethylene, ethylene which is obtained by a method, such as ethane dehydrogenation, ethanol dehydration, naphtha cracking, etc., can be used. Furthermore, a gas containing a lot of a hydrocarbon having a carbon atom number of 4, which is obtained by fluid catalytic cracking in which a fuel oil fraction obtained when a crude oil is distilled in the petroleum refining plant or the like is cracked in a fluidized bed state by using a powdered solid catalyst to convert it into a low boiling point hydrocarbon (the gas will be hereunder sometimes abbreviated as "FCC-C4"), may be used as the raw material gas, as it is or a gas obtained by removing impurities, such as phosphorus, arsenic, etc., from FCC-C4 may also be used as the raw material gas.

The main component as referred to herein means a component which is contained in an amount of typically 40% by volume or more, preferably 60% by volume or more, more preferably 75% by volume or more, and especially preferably 99% by volume or more relative to the raw material gas.

In addition, arbitrary impurities may be contained in the raw material gas for use in the present invention within a range where the effects of the present invention are not impaired. Specifically, in the case of producing butadiene from n-butene (1-butene and 2-butene), examples of the impurities which may be contained include branched monoolefins, such as isobutene, etc.; saturated hydrocarbons, such as propane, n-butane, i-butane, pentane, etc.; olefins, such as propylene, pentene, etc.; dienes, such as 1,2-butadiene, etc.; acetylenes, such as methylacetylene, vinylacetylene, ethylacetylene, etc.; and the like.

The amount of the impurities is typically 40% by volume or less, preferably 20% by volume or less, more preferably 10% by volume or less, and especially preferably 1% by volume or less. When this amount is excessively high, there is a tendency that the concentration of 1-butene or 2-butene as the main raw material decreases, so that the reaction becomes slow, or the yield of butadiene as the desired product is lowered.

In addition, in the present invention, although the concentration of the linear monoolefin having a carbon atom number of 4 or more in the raw material gas is not particularly limited, it is typically from 50.00 to 99.99% by volume, preferably from 55.00 to 99.9% by volume, and more preferably from 60.00 to 99.9% by volume.

<Oxidative Dehydrogenation Reaction Catalyst>

Next, the oxidative dehydrogenation reaction catalyst which is suitably used in the present invention is explained. The oxidative dehydrogenation reaction catalyst which is used in the present invention is preferably a composite oxide catalyst containing at least molybdenum, bismuth, and cobalt. Then, above all, a composite oxide catalyst represented by the following general formula (1) is more preferred.

$$Mo_a Bi_b Co_c Ni_d Fe_e X_f Y_g Z_h Si_i O_j \qquad (1)$$

In the formula, X is at least one element selected from the group consisting of magnesium (Mg), calcium (Ca), zinc (Zn), cerium (Ce), and samarium (Sm); Y is at least one element selected from the group consisting of sodium (Na), potassium (K), rubidium (Rb), cesium (Cs), and thallium (Tl); and Z is at least one selected from the group consisting of boron (B), phosphorus (P), arsenic (As), and tungsten (W).

Furthermore, a to j represent atomic proportions of the respective elements; when a=12, then b=0.5 to 7, c=0 to 10, d=0 to 10 (provided that (c+d)=1 to 10), e=0.05 to 3, f=0 to 2, g=0.04 to 2, h=0 to 3, and i=5 to 48; and j is a numerical value satisfying the oxidation states of other elements.

In addition, this composite oxide catalyst may be produced by a method of going through a step of integrating supply source compounds for the respective component elements constituting this composite oxide catalyst within an aqueous system and heating them. For example, all of the supply source compounds for the respective component elements may be integrated within an aqueous system and then heated. The supply source component as referred to herein means a compound containing a predetermined component element and is a compound capable of supplying the foregoing element as the catalyst by means of a ripening treatment as described later.

Above all, it is preferred that the composite oxide catalyst is produced by a method including a pre-step of heat treating an aqueous solution or aqueous water dispersion of raw materials compounds containing at least one selected from the group consisting of a molybdenum compound, an iron compound, a nickel compound, and a cobalt compound and silica, or a dry product obtained by drying this, to produce a catalyst precursor; and a post-step of integrating the catalyst precursor, a molybdenum compound, and a bismuth compound together with an aqueous solvent, followed by drying and calcination.

When the above-described method is adopted, the obtained composite oxide catalyst exhibits a high catalytic activity, and therefore, a conjugated diene, such as butadiene, etc., can be produced in a high yield, and a reaction product gas with a less content of an aldehyde can be obtained. The aqueous solvent as referred to herein means water, or an organic solvent having compatibility with water, such as methanol, ethanol, etc., or a mixture thereof.

Next, a production method of the composite oxide catalyst which is suitable in the present invention is explained.

First of all, in the production method of the composite oxide catalyst, it is preferred that the molybdenum which is used in the pre-step is molybdenum corresponding to an atomic proportion (a1) that is a part of the entire atomic proportion (a) of molybdenum, and the molybdenum which is used in the post-step is molybdenum corresponding to a remaining atomic proportion (a2) resulting from taking away a1 from the entire atomic proportion (a) of molybdenum. Then, the above-described a1 is preferably a value satisfying a relation of $\{1<a1/(c+d+e)<3\}$, and furthermore, the above-described a2 is preferably a value satisfying a relation of $\{10<a2/b<8\}$.

Examples of the supply source compound for the component element include an oxide, a nitrate, a carbonate, an ammonium salt, a hydroxide, a carboxylate, an ammonium carboxylate, a halogenated ammonium salt, a hydric acid, an acetyl acetonate, and an alkoxide of the component element, and the like. Specific examples thereof include the following compounds.

Examples of the supply source compound for Mo include ammonium paramolybdate, molybdenum trioxide, molybdic acid, ammonium phosphomolybdate, phosphomolybdic acid, and the like.

Examples of the supply source compound for Fe include ferric nitrate, ferric sulfate, ferric chloride, ferric acetate, and the like. Examples of the supply source compound for Co include cobalt nitrate, cobalt sulfate, cobalt chloride, cobalt carbonate, cobalt acetate, and the like.

Examples of the supply source compound for Ni include nickel nitrate, nickel sulfate, nickel chloride, nickel carbonate, nickel acetate, and the like. Examples of the supply source compound for Si include silica, granular silica, colloidal silica, fumed silica, and the like.

Examples of the supply source compound for Bi include bismuth chloride, bismuth nitrate, bismuth oxide, bismuth subcarbonate, and the like. In addition, the supply source compound for Bi can also be supplied as a composite carbonate compound of Bi and the X component (one or two or more of Mg, Ca, Zn, Ce, and Sm) or the Y component (one or two or more of Na, K, Rb, Cs, and Tl), in which the X component or the Y component is solid-solved.

For example, in the case of using Na as the Y component, a composite carbonate component of Bi and Na can be produced by mixing dropwise an aqueous solution of a water-soluble bismuth compound, such as bismuth nitrate, etc., with an aqueous solution of sodium carbonate or sodium bicarbonate, or the like and washing the obtained precipitate with water, followed by drying.

In addition, a composite carbonate compound of Bi and the X component can be produced by mixing dropwise an aqueous solution composed of bismuth nitrate and a water-soluble compound, such as a nitrate of the X component, etc., with an aqueous solution of ammonium carbonate or ammonium bicarbonate, or the like and washing the obtained precipitate with water, followed by drying.

When sodium carbonate or sodium bicarbonate is used in place of the above-described ammonium carbonate or ammonium bicarbonate, a composite carbonate compound of Bi, Na, and the X component can be produced. Examples of supply source compounds for other component elements include the following compounds.

Examples of the supply source compound for K may include potassium nitrate, potassium sulfate, potassium chloride, potassium carbonate, potassium acetate, and the like. Examples of the supply source compound for Rb may include rubidium nitrate, rubidium sulfate, rubidium chloride, rubidium carbonate, rubidium acetate, and the like.

Examples of the supply source compound for Cs include cesium nitrate, cesium sulfate, cesium chloride, cesium carbonate, cesium acetate, and the like. Examples of the supply source compound for Tl may include thallous nitrate, thallous chloride, thallium carbonate, thallous acetate, and the like.

Examples of the supply source compound for B may include borax, ammonium borate, boric acid, and the like. Examples of the supply source compound for P may include ammonium phosphomolybdate, ammonium phosphate, phosphoric acid, phosphorus pentoxide, and the like.

Examples of the supply source compound for As may include diarceno 18 ammonium molybdate, diarceno 18 ammonium tungstate, and the like. Examples of the supply source compound for W may include ammonium paratungstate, tungsten trioxide, tungstic acid, phosphotungstic acid, and the like.

Examples of the supply source compound for Mg include magnesium nitrate, magnesium sulfate, magnesium chloride, magnesium carbonate, magnesium acetate, and the like. Examples of the supply source compound for Ca include calcium nitrate, calcium sulfate, calcium chloride, calcium carbonate, calcium acetate, and the like.

Examples of the supply source compound for Zn include zinc nitrate, zinc sulfate, zinc chloride, zinc carbonate, zinc acetate, and the like. Examples of the supply source compound for Ce include cerium nitrate, cerium sulfate, cerium chloride, cerium carbonate, cerium acetate, and the like.

Examples of the supply source compound for Sm include samarium nitrate, samarium sulfate, samarium chloride, samarium carbonate, samarium acetate, and the like.

The aqueous solution or aqueous water dispersion of the raw material compound, which is used in the pre-step, is an aqueous solution, water slurry, or cake containing, as catalyst components, at least molybdenum (corresponding a1 out of the entire atomic proportion a), iron, at least either nickel or cobalt, and silica.

The aqueous solution or aqueous water dispersion of the raw material compound is prepared through integration of the supply source compounds in an aqueous system. Here, the integration of the supply source compounds of the respective component elements in an aqueous system means that aqueous solutions or aqueous water dispersions of supply source compounds of respective component elements are at least either mixed or ripened en bloc or stepwise.

That is, all of (a) a method of mixing the respective supply source compounds en bloc, (b) a method of mixing the respective supply source compounds en bloc and ripening the mixture, (c) a method of mixing stepwise the respective supply source compounds, (d) a method of repeating stepwise mixing/ripening of the respective supply source compounds, and a combination of (a) to (d) are included in the concept of integration of the supply source compounds of the respective component elements in an aqueous system.

Here, the ripening indicates an operation of treating the industrial raw material or half-finished product under a specified condition, such as a given time, a given temperature, etc., with an attempt to acquire or raise the required physical properties or chemical properties or allow the progress of a predetermined reaction. The given time is typically a range of 10 minutes to 24 hours, and the given temperature is typically a range of room temperature to the boiling point of the aqueous solution or aqueous water dispersion.

As for a specific method for the integration, examples thereof include a method in which a solution obtained by mixing acidic salts selected from the catalytic components and a solution obtained by mixing basic salts selected from the catalytic components are mixed, and the like, and specific examples thereof include a method of adding, under heating, a mixture containing an iron compound and at least either a nickel compound or cobalt compound to an aqueous solution of a molybdenum compound and then mixing silica therewith.

The thus obtained aqueous solution or aqueous water dispersion of the raw material compound containing silica is heated at 60 to 90° C. and ripened. The ripening as referred to herein means stirring of the slurry for catalyst precursor at a predetermined temperature for a predetermined time. By this ripening, the viscosity of the slurry increases, and sedimentation of a solid component in the slurry is relieved. This is effective especially in preventing disproportionation of the components in a next drying step. As a result, the catalytic activity, such as raw material conversion or selectivity of the composite oxide catalyst that is a final product to be obtained, etc., becomes more favorable.

The temperature at the ripening is typically from 60 to 100° C., preferably from 60 to 90° C., and more preferably from 70 to 85° C. By regulating the ripening temperature to 60° C. or higher, the effect for ripening becomes sufficient, and favorable activity is obtained, whereas by regulating it to 90° C. or lower, evaporation of water during the ripening time is suppressed, and such is advantageous for industrial practice. In addition, when the ripening temperature is 100° C. or lower, a pressure-resistant vessel becomes unnecessary for a dissolution tank, and the matter that handling becomes complicate is suppressed. Thus, the matter that the economy and operability become remarkably disadvantageous can be prevented from the occurring.

The time for which the ripening is applied is preferably from 2 to 12 hours, and more preferably from 3 to 8 hours. When the ripening time is 2 hours or more, the activity and selectivity of the catalyst are fully revealed. On the other hand, when the ripening time is 12 hours or less, the ripening effect is increased, and such is advantageous for industrial practice.

As the stirring method, an arbitrary method can be adopted, and examples thereof include a method by a stirrer having a stirring blade, a method by external circulation using a pump, and the like.

The ripened slurry is heat treated directly or after drying. In the case of drying the slurry, the drying method and the state of the obtained dry product are not particularly limited, and for example, a powdered dry product may be obtained using a usual spray drier, slurry drier, or drum drier, or the like, or a block-like or flake-like dry product may be obtained using a usual box-type drier or tunnel-type calcination furnace.

The aqueous solution of raw material salts or a granule or cake obtained by drying the aqueous solution is heat treated in air in a temperature region of typically from 200 to 400° C., and preferably from 250 to 350° C. for a short time. On that occasion, the form of the furnace and the method therefor are not particularly limited, and for example, heating may be performed using a usual box-type heating furnace or tunnel-type heating furnace or the like in a state where the dry product is fixed, or heating may also be performed using a rotary kiln or the like with fluidizing the dry product.

An ignition loss of the catalyst precursor obtained after the heat treatment is preferably from 0.5 to 5% by weight, and more preferably from 1 to 3% by weight. By regulating the ignition loss to this range, a catalyst having a high raw material conversion or selectivity can be obtained.

The ignition loss is a value obtained according to the following formula.

$$\text{Ignition loss (\%)}=[(W0-W1)/W0]\times 100$$

W0: Weight (g) after drying the catalyst precursor at 150° C. for 3 hours to remove the attached moisture.

W1: Weight (g) after further heat treating the catalyst precursor from which the attached moisture has been removed at 500° C. for 2 hours In the post-step, integration of the catalyst precursor obtained in the pre-step, a molybdenum compound (corresponding a2 remaining after subtracting corresponding a1 from the entire atomic proportion a), and a bismuth compound is performed in an aqueous solvent. On this occasion, it is preferred to add aqueous ammonia. It is also preferred that the addition of the X, Y, and Z components is performed in this post-step.

In addition, the bismuth supply source compound for use in the present invention is bismuth that is slightly soluble or insoluble in water. This compound is preferably used in a powder form. These compounds as raw materials for the catalyst production may be a particle larger than a powder, but taking into consideration a heating step in which heat should be diffused, a smaller particle is preferred. Accordingly, in the case where these compounds as raw materials are not such a small particle, pulverization should be performed before the heating step.

Subsequently, the obtained slurry is thoroughly stirred and dried. The thus obtained dry product is molded into an arbitrary shape by a method, such as extrusion molding, tablet molding, carrier molding, etc. Subsequently, the shaped product is preferably subjected to a final heat treatment under a temperature condition of 450 to 650° C. for approximately 1 to 16 hours. In this way, a composite oxide catalyst having high activity and giving the objective oxidation product in a high yield is obtained.

<Gas Containing Molecular Oxygen>

The gas containing molecular oxygen as referred to in the present invention means a gas containing molecular oxygen in an amount of typically 10% by volume or more, preferably 15% by volume or more, and more preferably 20% by volume or more, and specifically, air is preferred. From the viewpoint that the cost necessary for industrially preparing the gas containing molecular oxygen increases, an upper limit of the content of the molecular oxygen is typically 50% by volume or less, preferably 30% by volume or less, and more preferably 25% by volume or less. In addition, the gas containing molecular oxygen may contain arbitrary impurities within a range where the effects of the present invention are not impaired.

<Gas Supply>

In the present invention, at the time of supplying the raw material gas into the reactor, it is necessary to mix the raw material gas with the gas containing molecular oxygen and supply the gas after mixing (hereinafter sometimes referred to as a "mixed gas") to the reactor. In the mixed gas for use in the present invention, a proportion of the raw material gas is typically 3.0% by volume or more, preferably 5.0% by volume or more, and more preferably 6.0% by volume or more. There is a tendency that when this lower limit value becomes larger, the size of the reactor can be made smaller, and the costs involved in construction and operation are reduced. On the other hand, an upper limit thereof is typically 25.0% by volume or less, preferably 20.0% by volume or less, and more preferably 18.0% by volume or less. There is a tendency that when this upper limit value becomes smaller, the production of a high boiling point by-product is reduced.

In addition, a proportion of the linear monoolefin having a carbon atom number of 4 or more, such as n-butene (n-butene, such as 1-butene and/or 2-butene, etc.), etc., in the mixed gas is typically 1.0% by volume or more, preferably 3.0% by volume or more, and more preferably 5.0% by volume or more. On the other hand, an upper limit thereof is typically 20.0% by volume or less, preferably 16.0% by volume or less, and more preferably 14.0% by volume or less. When this proportion is less than 1.0% by volume, the amount of the obtained conjugated diene decreases, and hence, such is not preferred. In addition, when this proportion becomes larger, the amount of the obtained conjugated diene increases; however, coking is liable to be generated, and thus, the upper limit is more preferably 14.0% by volume or less.

<Reactor>

Although the reactor which is used for the oxidative dehydrogenation reaction for use in the present invention is not particularly limited, specifically, examples thereof include a tube-type reactor, a tank-type reactor, and a fluidized bed reactor. A fixed-bed reactor is preferred, a fixed-bed multitubular reactor or a plate-type reactor is more preferred, and a fixed-bed multitubular reactor is most preferred.

<Reaction Condition>

The oxidative dehydrogenation reaction for use in the present invention is an exothermic reaction, and the temperature increases by the reaction. However, in the present invention, the reaction temperature is regulated to a range of typically from 250 to 450° C., and preferably from 320 to 420° C. As this temperature becomes higher, the catalytic activity tends to be rapidly reduced, and as it becomes lower, the yield of the conjugated diene that is the objective product is liable to decrease. The reaction temperature can be controlled by using a heating medium (for example, dibenzyltoluene, a nitrite, etc.). The reaction temperature as referred to herein indicates the temperature of the heating medium.

In addition, although the temperature within the reactor for use in the present invention is not particularly limited, it is typically from 250 to 450° C., preferably from 320 to 450° C., and more preferably from 340 to 440° C. When the temperature of the catalyst layer is 450° C. or lower, as the reaction is continued, a lowering of the catalytic activity can be prevented from occurring. On the other hand, when the temperature of the catalyst layer is 250° C. or higher, a decrease of the yield of the conjugated diene that is the objective product can be prevented from occurring. The temperature within the reactor is determined according to the reaction condition and it can be controlled by a dilution ratio of the catalyst layer, a flow rate of the mixed gas, or the like. The "temperature within the reactor" as referred to herein indicates a temperature of the product gas at a reactor outlet, and in the case of a reactor having a catalyst layer, it indicates the temperature of the catalyst layer.

Although a pressure within the reactor for use in the present invention is not particularly limited, a lower limit thereof is typically 0 MPaG or more, preferably 0.001 MPaG or more, and more preferably 0.01 MPaG or more. As this value becomes larger, there is brought such an advantage that a larger amount of the reaction gas can be supplied into the reactor. On the other hand, an upper limit thereof is typically 0.5 MPaG or less, preferably 0.3 MPaG or less, and more preferably 0.1 MPaG or less. As this value becomes smaller, an explosion range tends to become narrower.

Although a residence time within the reactor for use in the present invention is not particularly limited, a lower limit thereof is typically 0.36 seconds or more, preferably 0.80 seconds or more, and more preferably 0.90 seconds or more. As this value becomes larger, there is brought such an advantage that the conversion of the monoolefin in the raw material gas becomes higher. On the other hand, an upper limit thereof is 3.60 seconds or less, preferably 2.80 seconds or less, and more preferably 2.50 seconds or less. As this value becomes smaller, the size of the reactor tends to become smaller.

2. Cooling Step (Hereinafter Sometimes Referred to "Quenching Step"):

A first invention in the present invention is explained. The first invention includes a cooling step of cooling the reaction product gas obtained in the above-described reaction step. In the cooling step, after supplying a cooling agent into a cooling column and bringing it into contact with the reaction product gas, the cooling agent discharged from the cooling column is cooled by a heat exchanger; a precipitate dissolved in the cooling agent is precipitated within the heat exchanger and recovered; and the cooling agent after recovering the precipitate is circulated into the cooling column. The cooling agent is preferably water.

<Cooling Column>

The cooling column for use in the present invention is aimed to rapidly cool the reaction product gas with the cooling agent. For that reason, the cooling column for use in the present invention is sometimes referred to as "rapid cooling column" or "quench column". In addition, the cooling agent is sometimes referred to as "quenchant".

In the present invention, the reaction product gas is introduced into the cooling column, water serving as the cooling agent is supplied into the cooling column, and in general, these are subjected to countercurrent contact with each other to lower the gas temperature. On this occasion, the reaction product gas is cooled to preferably 40° C. or lower, and more preferably 30° C. or lower. In other words, a column top temperature of the cooling column is regulated to preferably 40° C. or lower, and preferably 30° C. or lower.

In this way, a problem that the high boiling point by-product, such as fluorenone, etc., is precipitated within a piping or equipment continuing to the cooling column, or the like can be made hard to be generated. For example, when fouling is accumulated within a column top withdrawal pipe of the cooling column, or fouling is accumulated in the inside of a compressor on supplying the cooled product gas into the cooling column, there is a case where a problem, such as a decrease of discharge pressure of the compressor, etc., is generated.

When the reaction product gas is introduced into the cooling column, it is preferred to decrease the temperature in advance for cooling by a gas cooling heat exchanger. When the temperature of the reaction gas is high, there is a tendency that a load of a refrigerating machine, etc. necessary for cooling the gas by the cooling column, resulting in an increase in cost. On the other hand, when the reaction gas temperature is excessively decreased, there is a concern that a high boiling point by-product is deposed by the gas cooling heat exchanger. The temperature of the gas to be introduced into the cooling column is preferably from 300° C. to 130° C., and more preferably from 280° C. to 221° C.

The cooling column has preferably two or more cooling zones, and more preferably three or more cooling zones. Although an upper limit of the zone number is not particularly limited, it may be determined taking into consideration of a process cost, a cooling effect, or the like. Although a temperature of water serving as the cooling agent to be supplied into the cooling column is determined by a temperature of the product gas, a proportion of the product gas and water, or the like, it is typically from 10 to 90° C., preferably from 10 to 70° C., and more preferably from 10 to 60° C.

In the method according to the present invention, with respect to the plural cooling zones, water is supplied as the cooling agent into the cooling column; the water serving as the cooling agent, which has been withdrawn from a lowermost stage of each of the zones, is generally circulated into an upper part than the withdrawal position (circulating water) and after cooling of the reaction product gas and removal of the reaction by-product are performed, becomes a withdrawal liquid of each zone, if desired. However, in the present invention, with respect to the cooling zones other than the lowermost part of the plural zones of the cooling column, the cooling agent is cooled by the heat exchanger at an appropriate temperature of typically from 10 to 90° C., preferably from 10 to 70° C., and more preferably from 10 to 60° C. and then circulated.

From the viewpoint of suppressing precipitation of a high boiling point by-product, it is preferred that with respect to the water (in which a minute amount of fluorenone is dissolved) serving as the cooling agent withdrawn from the cooling zone of the lowermost part of the cooling column, a part thereof is circulated into the cooling column without cooling a part thereof, and the remainder is purged out the system.

The water and circulating water serving as the cooling agent have a pH of preferably 3 to 11, and more preferably from 6 to 8. In addition, the cooling agent is preferably water, and more preferably water having a pH of 6 to 8. A flow rate of the circulating water of the cooling column may be appropriately set up according to the temperature at which the reaction product gas is cooled, the amount of the by-product to be removed, or the size or stage number of the cooling column.

Examples of the heat exchanger that cools the circulating water include a multitubular heat exchanger, a plate-type heat exchanger, a spiral-type heat exchanger, and the like. Of these, a multitubular heat exchanger is preferred. In the case of using a multitubular heat exchanger, it is preferred to flow a circulating water (cooling agent) on the tube side and a cooling medium (for example, water or brain) on the body side, respectively. In the multitubular heat exchanger, a temperature difference between the circulating water on the tube side and the cooling medium on the body side is preferably from 70 to 20° C.

Although the high boiling point by-product, particularly 9-fluorenone is generally slightly soluble in water, its production amount is minute, and it is not meant that the 9-fluorenone is quite insoluble in water. Thus, by bringing the cooling agent and the reaction product gas into contact with each other, the 9-fluorenone can be dissolved in water serving as the cooling agent. Thereafter, by cooling the cooling agent discharged from the cooling column by a heat exchanger or the like, the 9-fluorenone dissolved in the cooling agent can be precipitated as a precipitate. The precipitated 9-fluorenone can be separated from the cooling agent by the heat exchanger or the like.

Namely, it is possible to separate the high boiling point by-product by using a difference of its solubility in water. Specifically, assuming cooling crystallization, (F×ΔC/100) obtained by multiplying a flow rate F (kg/h) of the liquid by a solubility difference ΔC (wt %) between an inlet and an outlet of a crystallizer is a precipitation amount per unit time.

As a preferred embodiment of the first invention, two or more of the heat exchangers are provided in parallel. According to this, by precipitating the high boiling point by-product, particularly 9-fluorenone on a heat transfer surface of the heat exchanger, exchanging and using the heat exchanger, and cleaning up the non-used heat exchanger, the high boiling point by-product, particularly 9-fluorenone can be efficiently removed (see FIG. 2).

In addition, as another preferred embodiment, one heat exchanger and a bypass piping are provided, the cooling agent discharged from the cooling column is passed through the heat exchanger, or as occasion demands, the cooling agent is passed through the heat exchanger and the bypass piping, and 9-fluorenone is precipitated within the heat exchanger and then recovered. During cleaning up the heat exchanger, the cooling agent is passed through the bypass piping (see FIG. 3).

In these cases, a liquid linear rate of the cooling agent (circulating water) passing through the heat exchanger is preferably 1.0 m/sec or less, more preferably 0.5 m/sec or less, and still more preferably 0.2 m/sec or less. According to this, the amount of the high boiling point by-product precipitated within the heat exchanger, particularly 9-fluorenone increases, and the removal efficiency of the high boiling point by-product, particularly 9-fluorenone is improved. As a method of varying the liquid linear rate, for example, a known method, such as varying a tube diameter of the heat exchanger, etc., may be adopted.

When the liquid linear rate of the circulating water is 1.0 m/sec or less, the circulating water is hardly suspended, and the high boiling point by-product is readily precipitated within the heat exchanger, so that the matter that the high boiling point by-product floats in the circulating water to be circulated into the cooling column can be prevented from occurring. According to this, the high boiling point by-product to be circulated into the cooling column increases and is suppressed from its accumulation within the piping or cooling column, whereby fouling or clogging can be prevented from occurring.

The cooling column preferably has 2 to 3 cooling zones. In the cooling zone or zones other than the lowermost part, it is preferred that two or more of the heat exchangers are provided, and it is more preferred that two or more of the heat exchangers are provided in at least either a parallel direction or a series direction. In addition, in the cooling step, the reaction product gas is cooled to preferably 40° C. or lower, more preferably from 35 to 10° C., and more preferably from 30 to 20° C.

According to this, transpiration of the high boiling point by-product, particularly 9-fluorenone from the column top of the cooling column can be reduced, and its accumulation within the piping or pump or the like, through which an effluent gas from the column top of the cooling column passes, can be suppressed.

Since the amount of the high boiling point by-product precipitated within the heat exchanger is minute, the heat exchanger may be operated until usual periodic maintenance without remarkably decreasing a heat transfer coefficient thereof. In this case, the high boiling point by-product precipitated within the heat exchanger is removed when the operation is stopped.

Alternatively, in the case where the heat transfer coefficient of the heat exchanger is decreased due to the high boiling point by-product precipitated within the heat exchanger, it is possible to perform the continuous operation by installing a spare heat exchanger installed in parallel and switching it, or washing the heat exchanger during a period of passing the liquid through the bypass piping. An embodiment in which the high boiling point by-product is removed from the stopped heat exchanger, and the resulting heat exchanger is remained until next switching is preferred.

In addition, in the first invention, it is also preferred to preliminarily cool the cooling agent discharged from the cooling column after its contact with the reaction product gas by a condenser, such as a heat exchanger, etc., and then precipitate the precipitate dissolved in the cooling agent within a different heat exchanger from the preliminarily cooled condenser. A linear rate of the cooling agent passing through the inside of the condenser for preliminary cooling is preferably faster than 1.0 m/sec for the purpose of suppressing accumulation of the precipitate.

According to the first invention, in view of the fact of obtaining a concept that not only the circulating water is cooled by using the heat exchanger at a low liquid linear rate, but also the high boiling point by-product is precipitated by the heat exchanger and separated from the circulating water, it becomes possible to achieve the separation of the high boiling point by-product.

Although a concentration of the high boiling point by-product to be precipitated by the heat exchanger in the circulating water (cooling agent to be circulated into the cooling column) cannot be unequivocally prescribed since it varies depending upon the production amount by the reaction, or the condition of the cooling column, according to the investigations made by the present inventors, fouling of the cooling column can be efficiently prevented from occurring so long as the concentration of 9-fluorenone in the circulating water (cooling agent to be circulated into the cooling column) is preferably regulated to 30 ppm by weight or less.

Although a preferred embodiment of the first invention is specifically explained below by reference to FIG. 2, it should be construed that the present invention is not limited thereto.

Figure 2:
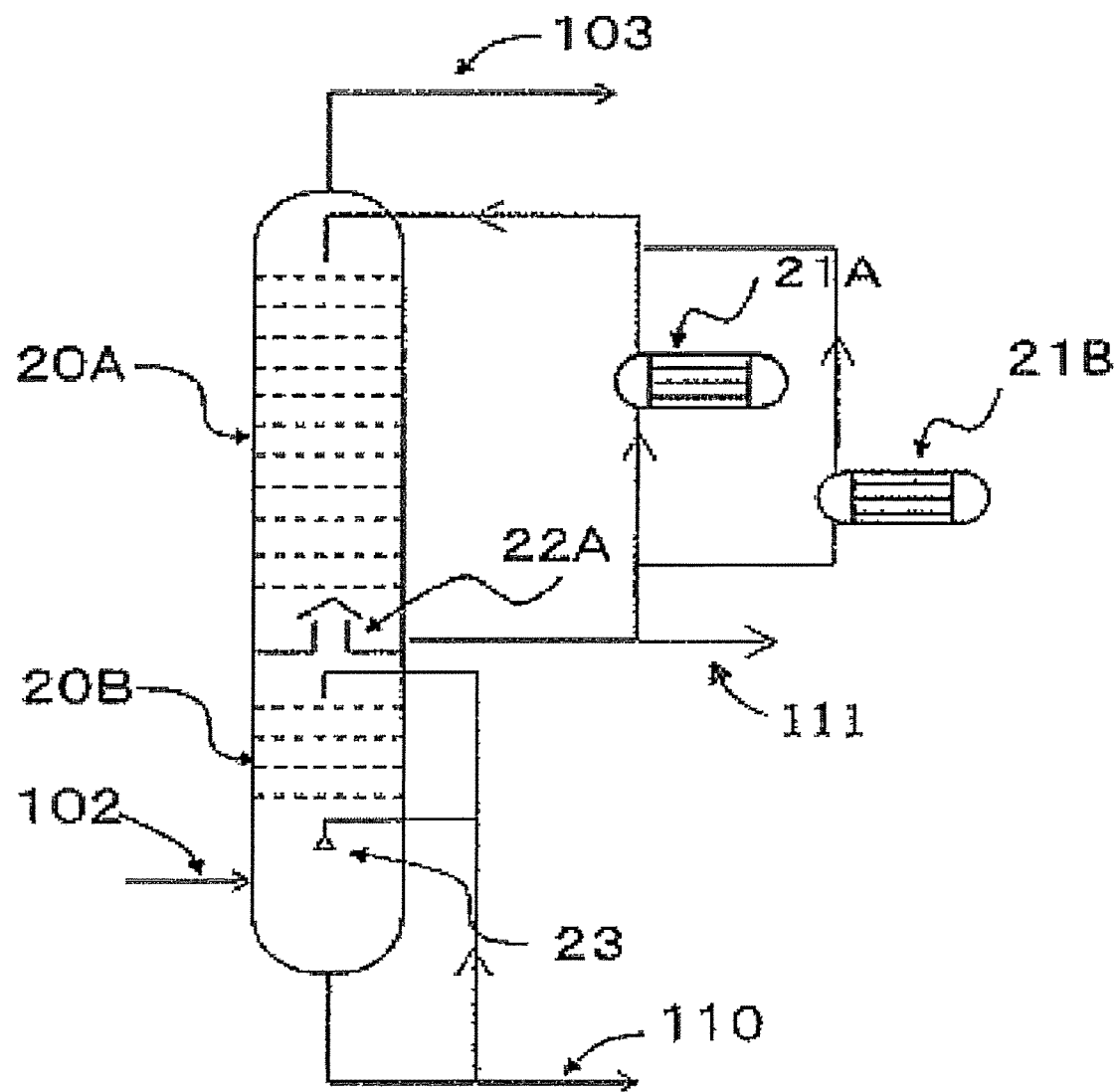
FIG. 2 is a view diagrammatically showing an example of a cooling column to be used for a mode for carrying out a method for producing a conjugated diene according to the present invention.

FIG. 2 shows an example of a cooling column to be used for a method for producing a conjugated diene according to the present embodiment. This cooling column is an example including three zones, and a chimney 22A is provided in the middle thereof. One zone is formed by a tray 20A; one zone is formed by a tray 20B; and one ozone is formed by a space in a lower part of a water spray apparatus 23. The chimney 22A is opened in the center, and the opening is provided with an upwardly projected weir. As shown in FIG. 2, the circulated circulating water remains in trays integrally installed on the chimney 22A and flows out into a circulation passage.

The flown-out circulating water is supplied into a heat exchanger 21A; cooled to a desired temperature; and then circulated and used. On this occasion, the moisture contained in the reaction product gas is cooled and condensed by the cooling column, and a liquid level within the chimney weir becomes high. Thus, by continuously withdrawing the resulting liquid so as to keep the liquid level constant, the withdrawn water may be sent to a zone beneath the chimney (not shown), or by installing a tank, etc. (not shown) on the way of the liquid circulation passage, the resulting liquid may be withdrawn out the system of wastewater processing equipment or the like so as to keep the liquid level of the tank, etc. constant.

By cooling the circulating water by the heat exchanger 21A, the high boiling point by-product, such as 9-fluorenone, etc., is precipitated on the cooling surface of the heat exchanger. When the precipitation amount becomes large, the cooling efficiency is lowered, or the circulating water hardly flows, and thus, the passage of the circulating water is changed from the heat exchanger 21A to a heat exchanger 21B.

It is possible to remove the high boiling point by-product precipitated on the cooling surface of the heat exchanger 21A by a known method. Examples thereof include scraping of the precipitate on the cooling surface using a brush, high-pressure water washing, dissolution under heating at a melting point of the precipitate or high, and the like. In addition, for example, it is also possible to achieve washing with an appropriate solvent. Then, when the high boiling point by-product becomes accumulated on the cooling surface of the heat exchanger 21B, the passage of the circulating water is changed to the heat exchanger 21A, and the high boiling point by-product precipitated by the heat exchanger 21B is removed.

In this way, by using the plural heat exchangers with successively switching, the high boiling point by-product produced by the reaction can be precipitated on the cooling surface of the heat exchanger and removed, and the matter that the cooling column is fouled, or the fouling substance flows out into the post-step to hinder the operation, can be prevented from occurring.

A second invention in the present invention is explained. In a cooling step of cooling the reaction product gas obtained in the above-described reaction step, the cooling agent is supplied into a cooling column and brought into contact with the reaction product gas; the cooling agent discharged from the cooling column is then cooled by a condenser; a precipitate precipitated by cooling is then recovered by a separation apparatus; and the cooling agent after recovery of the precipitate is circulated into the cooling column. In this way, the high boiling point by-product, particularly 9-fluorenone is precipitated in the circulating water and captured by the separation apparatus in a state that it floats in the circulating water.

The cooling column is the same as in the first invention. Water is preferred as the cooling agent. In the second invention, although the condenser is not particularly limited, a heat exchanger is preferred. A liquid linear rate of the cooling agent passing through the heat exchanger is preferably faster than 1.0 m/sec (more than 1.0 m/sec); more preferably 1.5 m/sec or more; and still more preferably 2.0 m/sec or more.

When the liquid linear rate of the circulating water is faster than 1.0 m/sec, the precipitated high boiling point by-product is hardly attached onto the heat transfer surface within the heat exchanger, and the operating time of the heat exchanger can be made longer. In addition, for the same reason as described above, it is preferred that the reaction product gas is cooled to 40° C. or lower in the cooling step; a cooling column having two or more cooling zones is used; and the second method according to the present invention is carried out in a cooling zone other than the lowermost part.

The above-described separation apparatus is also called a high boiling point by-product separation apparatus and installed for the purpose of separating a high boiling point by-product as described later. It is preferred that two or more separation apparatuses are provided. Examples of the separation apparatus include screen, gravity settling, gravity filtration, floatation, vacuum filtration, pressure filtration, cyclone, centrifugal settling machine, centrifugal filtration machine, and the like. Among them, screen and centrifugal filtration machine are preferred, and screen is more suitably used. In particular, a screen built-in strainer is preferred.

In the case where the separation apparatus is a screen built-in strainer, the screen preferably has a size of 100 to 200 mesh. Examples of the material include a metal and a resin, wherein a metal being preferred. In this way, in particular, 9-fluorenone may be efficiently removed.

Since the amount of the high boiling point by-product separated within the separation apparatus is minute, the separation apparatus may be operated until usual periodic maintenance without remarkably increasing a pressure loss of the separation apparatus. In this case, the high boiling point by-product separated within the separation apparatus is removed when the operation is stopped.

Alternatively, in the case where the pressure loss of the separation apparatus is increased due to the high boiling point by-product separated within the separation apparatus, it is possible to perform the continuous operation by installing a spare separation apparatus and switching it. On the other hand, an embodiment in which the high boiling point by-product is removed from the stopped separation apparatus, and the resulting separation apparatus is remained until next switching is also preferred.

Namely, according to the second invention, in view of the fact of obtaining a concept that after the cooling agent is cooled at a high liquid linear rate by the heat exchanger, the precipitated high boiling point by-product is separated from the circulating water in the separation apparatus in the downstream without being attached to the heat exchanger, by which it becomes possible to separate the high boiling point by-product.

Although a concentration of the high boiling point by-product to be precipitated by the heat exchanger in the circulating water (cooling agent to be circulated into the cooling column) cannot be unequivocally prescribed because it varies depending upon the production amount by the reaction, or the condition of the cooling column, according to the investigations made by the present inventors, there is a tendency that fouling of the cooling column can be efficiently prevented from occurring by regulating the concentration of 9-fluorenone in the circulating water (cooling agent to be circulated into the cooling column) to 30 ppm by weight or less.

Figure 4:
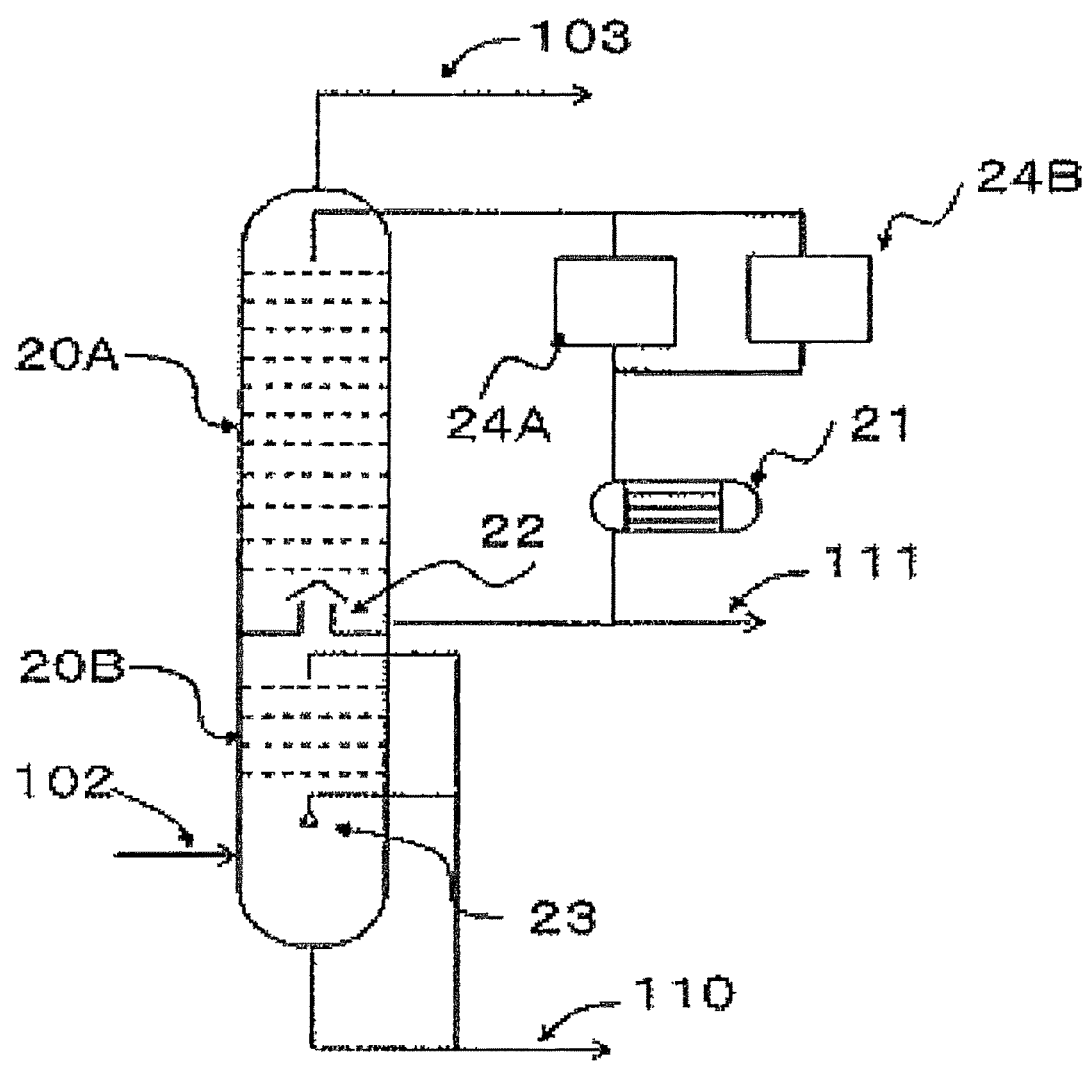
FIG. 4 is a view diagrammatically showing an example of a cooling column to be used for a mode for carrying out a method for producing a conjugated diene according to the present invention.

Although the second invention is specifically explained below by reference to FIG. 4, it should be construed that the present invention is not limited thereto. FIG. 4 shows an example of a cooling column to be used for a method for producing a conjugated diene according to the present embodiment. This cooling column is an example including three zones, and a chimney 22 is provided in the middle thereof. The chimney 22 is opened in the center, and the opening is provided with an upwardly projected weir.

As shown in FIG. 4, the circulated circulating water remains in trays integrally installed on the chimney 22 and flows out into a circulation passage. The flown-out circulating water is supplied into a heat exchanger 21, cooled to a desired temperature, and then circulated and used. On this occasion, the moisture contained in the reaction product gas is cooled and condensed by the cooling column, and a liquid level within the chimney weir becomes high. Thus, by continuously withdrawing the resulting liquid so as to keep the liquid level constant, the withdrawn water may be sent to a zone beneath the chimney (not shown), or by installing a tank, etc. (not shown) on the way of the liquid circulation passage, the resulting liquid may be withdrawn out the system of wastewater processing equipment or the like so as to keep the liquid level of the tank, etc. constant.

By cooling the circulating water by the heat exchanger 21, the high boiling point by-product, such as 9-fluorenone, etc., is precipitated as a solid in the circulating water. The circulating water containing the precipitated high boiling point by-product containing 9-fluorenone, etc. which has come out from the heat exchanger 21 is separated into the circulating water and the precipitated high boiling point product containing 9-fluorenone, etc. by a separation apparatus 24A. The circulating water from which the precipitated high boiling point product containing 9-fluorenone, etc. is separated is circulated into the cooling column.

When the separated amount becomes increased, the circulating water becomes to hardly flow, and the pressure loss of the separation apparatus 24A increases, and thus, the passage of the circulated water is changed from the separation apparatus 24A to a separation apparatus 24B. It is possible to remove the high boiling point by-product attached to a separation surface of the separation apparatus 24A by a known method. Examples thereof include scraping of the precipitate on the separation surface using a brush, high-pressure water washing, dissolution under heating at a melting point of the precipitate or high, and the like. In addition, it is also possible to achieve washing with an appropriate solvent.

Then, when the high boiling point by-product becomes accumulated on the separation surface of the separation apparatus 24B, the passage of the circulating water is changed to the separation apparatus 24A, and the high boiling point by-product accumulated in the separation apparatus 24B is removed. In this way, by using the plural high boiling point product separation apparatuses with successively switching, the high boiling point by-product produced by the reaction can be separated and removed by the high boiling point product separation apparatus without being precipitated on the cooling surface of the heat exchanger, and the matter that the cooling column is fouled, or the fouling substance flows out into the post-step to hinder the operation, can be prevented from occurring.

<Embodiment of Process>

An embodiment of a process regarding the method for producing a conjugated diene according to the present invention is hereunder explained with respect to an example of producing butadiene by reference to the drawings.

FIG. 1 is one mode for carrying out of the process according to the present invention. In FIG. 1, 1 denotes a reactor; 2 denotes a gas cooling heat exchanger; 3 denotes a cooling column; 4 denotes a compressor; 5 denotes an absorption column; 6 denotes a deaeration column; and 7 denotes a solvent separation column.

Figure 3:
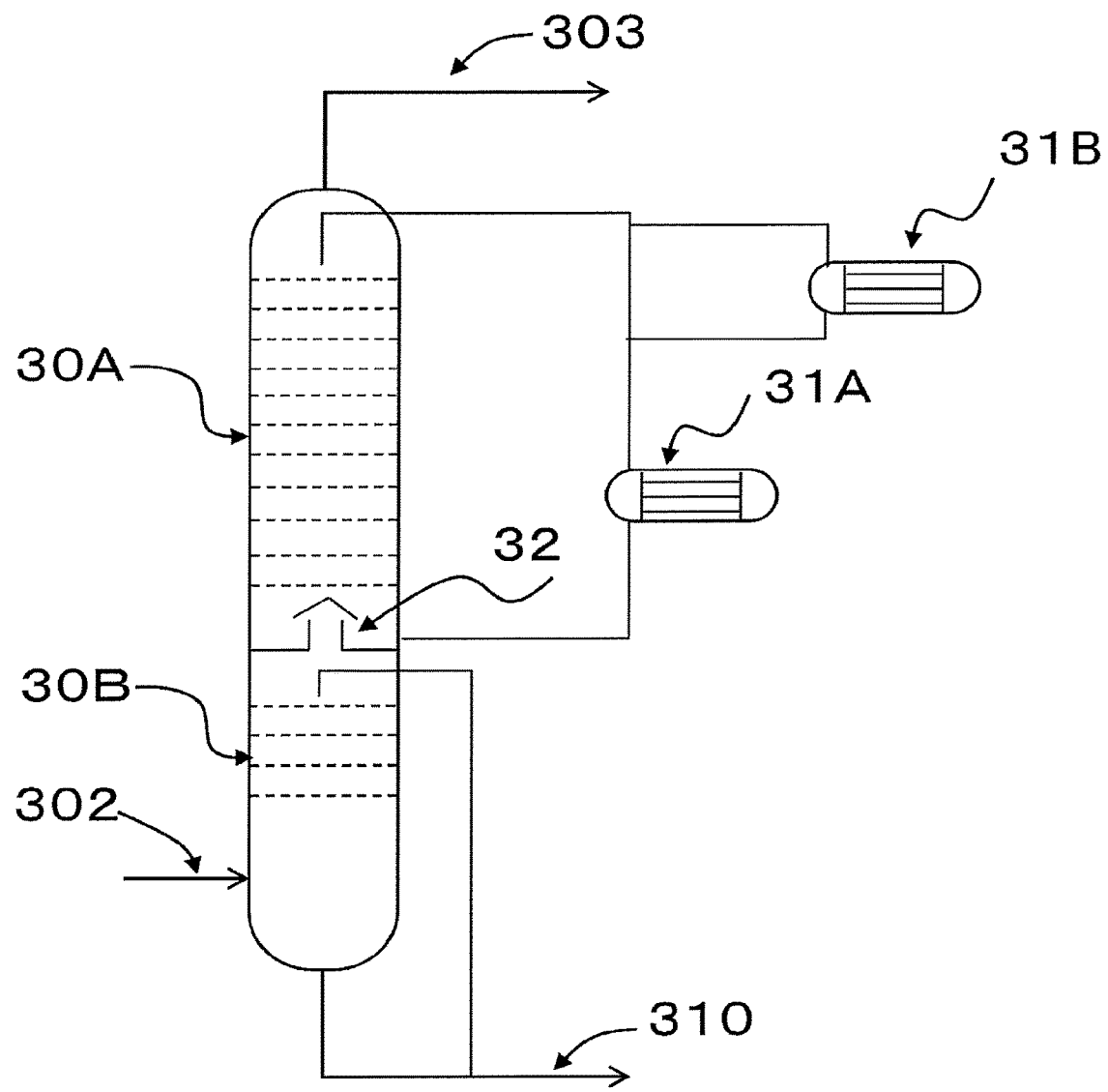
FIG. 3 is a view diagrammatically showing an example of a cooling column to be used for a mode for carrying out a method for producing a conjugated diene according to the present invention.

FIGS. 2 and 3 are each one mode of the cooling column 3; 20A, 20B 30A, and 30B each denote a tray or packing layer; 21A, 21B, 31A, and 31B each denote a heat exchanger; 22A and 32 each denote a chimney; and 23 denotes a water spray apparatus. In FIGS. 1, 2, and 3, 100 to 111, 302, 303, and 310 each denote a piping.

FIG. 4 is one mode of the cooling column 3; 20A and 20B each denote a tray or packing layer; 21 denotes a heat exchanger; 22 denotes a chimney; 23 denotes a water spray apparatus; and 24A and 24B each denote a separation apparatus (high boiling point by-product separation apparatus). In FIGS. 4, 102 to 103, 110, and 111 each denote a piping.

FIG. 1 shows a method for producing a conjugated diene by using, as a raw material gas, BBSS that is a component discharged from an extraction separation process of butadiene from a C4 fraction which is formed as a by-product in naphtha cracking and using butadiene as a conjugated diene to be obtained. n-Butene serving as a raw material or a mixture containing n-butene, such as the above-described BBSS, etc., is gasified by a vaporizer (not shown) and, after heating a mixed gas of a nitrogen gas, air (gas containing molecular oxygen), and water (steam) at appropriately 150 to 400° C. by a preheater (not shown), is supplied into the multitubular reactor 1 (oxidative dehydrogenation reactor) packed with a catalyst via the piping 100.

The reaction product gas from the reactor 1 is withdrawn via the piping 101; cooled by the gas cooling heat exchanger 2; then introduced into the cooling column 3 from the column bottom via the piping 102; and then subjected to countercurrent contact with the circulating water, whereby the high boiling point by-product is dissolved and separated. The reaction gas from which the high boiling point by-product has been removed is discharged from the piping 103.

The discharged gas is compressed by the compressor 4, supplied into the absorption column 5, and then subjected to countercurrent contact with an absorption solvent from the piping 104. According to this, the conjugated diene or unreacted raw material gas in the reaction product gas is absorbed in the absorption solvent.

A component (off gas) which has not been absorbed in the absorption solvent is withdrawn from the column top of the absorption column via the piping 105, and at least a part thereof is circulated into the reactor. On this occasion, at least a part of an organic substance or carbon monoxide in the off gas may be converted into carbon dioxide and then circulated into the reactor.

The absorption solvent having the conjugated diene or raw material gas dissolved therein is withdrawn from the bottom of the absorption column 5 and then sent to the deaeration column 6 via the piping 106. In the deaeration column, oxygen, nitrogen, carbon dioxide, and the like having been dissolved in minute amounts in the absorption solvent are gasified and then removed. On this occasion, since the butadiene or raw material, and a part of the absorption solvent may be possibly gasified, it is suitable that these are liquefied by a condenser (not shown) provided in the column top of the deaeration column and then recovered into the absorption solvent via the piping 107.

The absorption solvent in which the conjugated diene or raw material gas withdrawn from the column bottom of the deaeration column has been dissolved is supplied into the solvent separation column 7 via the piping 108. In the solvent separation column 7, distillation separation of the conjugated diene is performed, and a crude butadiene fraction is withdrawn from the column top via the piping 109.

The separated absorption solvent is withdrawn from the column bottom via the piping 104 and circulated and used as the absorption solvent of the absorption column 5. In addition, on performing circulation, it is preferred that impurities accumulated in the solvent are separated by a method, such as distillation, etc. (not shown), followed by circulation.

Although the present invention is hereunder explained in more detail by reference to the following Examples, it should be construed that the present invention is by no means limited by the Examples described below.

EXAMPLES

[Preparation Example 1] (Preparation of Composite Oxidative Catalyst)

In 250 mL of pure water, 54 g of ammonium paramolybdate was dissolved under heating at 70° C. Subsequently, 7.18 g of ferric nitrate, 31.8 g of cobalt nitrate, and 31.8 g of nickel nitrate were dissolved in 60 mL of pure water under heating at 70° C. These solutions were gradually mixed with thoroughly stirring.

Subsequently, 64 g of silica was added, and the contents were thoroughly stirred. This slurry was heated at 75° C. and ripened for 5 hours. Thereafter, this slurry was dried under heating and then heat-treated at 300° C. for one hour in an air atmosphere.

The resulting particulate solid (ignition loss: 1.4% by weight) of the catalyst precursor was pulverized, and 40.1 g of ammonium paramolybdate was dispersed in a solution obtained by adding and dissolving 10 mL of aqueous ammonia in 150 ml of pure water. Subsequently, 0.85 g of borax and 0.36 g of potassium nitrate were dissolved in 40 mL of pure water under heating at 25° C., and the resulting solution was added to the above-described slurry.

Subsequently, 58.1 g of bismuth subcarbonate having 0.45% of Na solid-solved therein was added and mixed with stirring. The resulting slurry was dried under heating at 130° C. for 12 hours, and the obtained particulate solid was subjected to tablet molding into a tablet of 5 mm in diameter and 4 mm in height by using a small molding machine and then calcined at 500° C. for 4 hours to obtain a catalyst.

The catalyst was a composite oxide having the following atomic proportion as calculated from the charged raw materials.

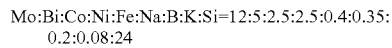

Mo:Bi:Co:Ni:Fe:Na:B:K:Si=12:5:2.5:2.5:0.4:0.35: 0.2:0.08:24

In addition, the atomic proportions a1 and a2 of molybdenum on the occasion of preparation were 6.9 and 5.1, respectively.

Example 1

In a reaction tube inside the reactor 1 equipped with 113 reaction tubes each having an inner diameter of 27 mm and a length of 3,500 mm, 309 mL of the composite oxide catalyst produced in Production Example 1 and 398 mL of an inert ball (manufactured by Tipton Corp.) were packed per reaction tube. At this time, the catalytic layer was configured of three layers, and dilution ratios of the respective layers in the direction from the reactor inlet toward the product gas outlet of the reactor were 80% by volume, 60% by volume, and 25% by volume, respectively.

A raw material gas having a component composition shown in the following Table 1, which was discharged from the extraction separation process of butadiene from the C4 fraction formed as a by-product in naphtha cracking, air, nitrogen, and steam were supplied into a preheater in flow rates of 15.9 Nm$^3$/h, 87.5 Nm$^3$/h, 55.9 Nm$^3$/h, and 17.7 Nm$^3$/h, respectively and heated at 217° C., and then supplied into a multitubular reactor from a raw material gas inlet.

A coolant at a temperature of 380° C. was flown into the body side of the reactor, thereby regulating a maximum temperature of the inside of the reaction tube to 412 to 415° C. The product gas withdrawn from the reactor was supplied into the cooling column, and the composition of the product gas was measured in the outlet of the cooling column and found as shown in the following Table 2.

The cooling column is a 30-stage sieve tray column having an inside diameter of 304 mm as shown in FIG. 2, and the chimney is installed between the 20th stage and the 21st stage from above.

TABLE 1

| ComponentNname | Composition (mol %) |
|---|---|
| n-Butane | 12.2 |
| i-Butane | 2.2 |
| 1-Butene | 45.4 |
| Cis-2-butene | 15.9 |
| Trans-2-butene | 19.9 |
| Other components | 4.4 |

TABLE 2

| Component Name | Composition (mol %) |
|---|---|
| Butadiene | 5.77 |
| Nitrogen | 66.6 |
| Oxygen | 5.42 |
| H$_2$O | 17 |
| Other components | 5.21 |

An effluent gas from the column top of the cooling column was subjected to pressure rising to 0.35 MPaG (gauge pressure, hereinafter the same) by the two-stage type compressor 4 and introduced into the absorption column 5. A part of an effluent from the column bottom of the cooling column was circulated into the water spray apparatus 23 at a rate of 1,000 kg/h. Furthermore, the effluent was circulated into the lower part of the chimney at a rate of 1,000 kg/h.

An effluent water from the chimney was sent to the heat exchanger 21A at a rate of 1,000 kg/h. The heat exchanger 21A was configured of 18 tubes each having an outside diameter of 19 mm, a thickness of 1.65 mm, and a length of 4 m; circulating water was flown into the tubes; and cooling water at 5° C. was flown into the outside (body side) of the tubes. An inlet temperature of the circulating water of the heat exchanger 21A was 50° C., and an outlet temperature was regulated to 25° C. by an amount of the cooling water. A liquid linear rate within the tube was 8 cm/sec (0.08 m/sec).

Although the amount of the cooling water of the heat exchanger 21A at the time of starting the operation was 460 kg/h, it rose to 1,600 kg/h after 2 weeks. Thus, the passage was switched to the heat exchanger 21B having exactly the same structure as the heat exchanger 21A; cooling of the circulating water was performed by using the heat exchanger 21B; and the operation was continued for 2 weeks. During this, the heat exchanger 21A was left open, and a precipitate attached within the tubes was cleaned up with a brush.

In this way, a switching operation between the heat exchangers 21A and 21B at an interval of 2 weeks was performed for 2 months. During this, a concentration of 9-fluorenone in the circulating water was 17 ppm by weight, and the column top temperature of the cooling column remained constant at 25° C. In addition, a one-stage discharge pressure and a two-stage discharge pressure of the compressor 4 remained stable at 0.15 MPaG and 0.35 MPaG; respectively. In addition, the weight of the precipitate recovered by washing of the heat exchangers was 485 g per two weeks in average.

Example 2

In one reaction tube having an inside diameter of 27 mm and a length of 6,000 mm, 309 mL of the composite oxide catalyst produced in Production Example 1 and 398 mL of an inert ball (manufactured by Tipton Corp.) were packed. At this time, the catalytic layer was configured of three layers, and dilution ratios of the respective layers in the direction from the reactor inlet toward the product gas outlet of the reactor were 80% by volume, 60% by volume, and 25% by volume, respectively.

A raw material gas having a component composition shown in the foregoing Table 1, which was discharged from the extraction separation process of butadiene from the C4 fraction formed as a by-product in naphtha cracking, air, nitrogen, and steam were supplied into a preheater in flow rates of 0.14 Nm$^3$/h, 0.77 Nm$^3$/h, 0.49 Nm$^3$/h, and 0.16 Nm$^3$/h, respectively and heated at 120° C., and then supplied into a multitubular reactor from a raw material gas inlet.

A coolant at a temperature of 380° C. was flown into the body side of the reactor, thereby regulating a maximum temperature of the inside of the reaction tube to 412 to 415° C. The product gas withdrawn from the reactor was supplied into the cooling column, and the composition of the product gas was measured in the outlet of the cooling column. As a result, it was found to have the same values shown in the foregoing Table 2.

The cooling column is a 19-stage dual flow tray column having an inside diameter of 54 mm as shown in FIG. 3, and the chimney is installed between the 9th stage and the 10th stage from above. An effluent gas from the column top of the cooling column shown in FIG. 3 was sent to a flare. An effluent from the column bottom of the cooling column was circulated into the lower part of the chimney at a rate of 12 kg/h.

An effluent water from the chimney was sent to the heat exchanger 31A at a rate of 12 kg/h and sent to the heat exchanger 31B at a rate of 6 kg/h. The heat exchanger 31A was configured of one tube having an outside diameter of 10 mm, a thickness of 1 mm, and a length of 0.8 m; circulating water was flown into the tube; and cooling water at 5° C. was flown into the outside (body side) of the tube. An inlet temperature of the circulating water of the heat exchanger 31A was 70° C., and an outlet temperature was regulated to 50° C. by an amount of the cooling water. A liquid linear rate within the tube of the heat exchanger 31A was 0.066 m/sec.

The heat exchanger 31B was configured of one tube having an outside diameter of 10 mm, a thickness of 1 mm, and a length of 1.4 m; circulating water was flown into the tube; and cooling water at 5° C. was flown into the outside (body side) of the tube. An inlet temperature of the circulating water of the heat exchanger 31B was 50° C., and an outlet temperature was regulated to 30° C. by an amount of the cooling water. A liquid linear rate within the tube of the heat exchanger 31B was 0.033 m/sec.

After operating the heat exchangers 31A and 31B for 144 hours, the heat exchanger 31B was left open, and a precipitate attached within the tube was cleaned up with a brush. 9-Fluorenone was precipitated in an amount of 12.8 mg/h.

Reference Examples 1 to 5: Confirmation Test of Precipitation of High Boiling Point By-Product In the above-described Examples in which water was used as the cooling agent, and the cooling agent was cooled by the heat exchanger and circulated into the cooling column, in order to verify a relation between the liquid linear rate of the cooling agent passing through the heat exchanger and the precipitation of the high boiling point by-product contained in the cooling agent onto the cooling transfer surface of the heat exchanger (fouling on the cooling transfer surface), the following test was performed.

Figure 5:
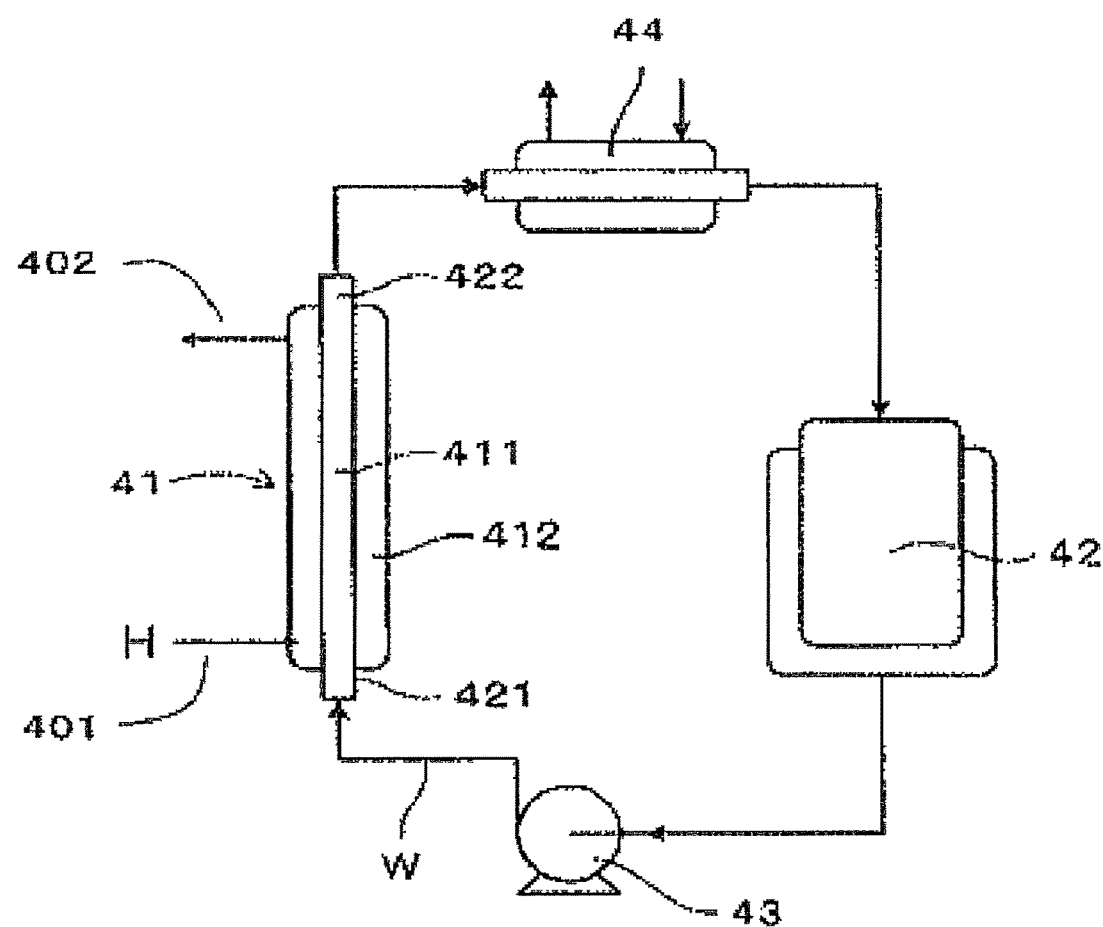
FIG. 5 is a fouling evaluation heat exchanger unit to be used for a confirmation test of a method for producing a conjugated diene according to the present invention.

That is, a precipitation rate of the high boiling point by-product onto the cooling transfer surface was measured with using a fouling evaluation heat exchanger unit shown in FIG. 5. A test heat exchanger 41 was a single-tube double-pipe heat exchanger using a test heat exchanger tube 411 having an outside diameter of 12.7 mmφ, a thickness of 1.2 mm, and a length of 500 mm, and a drawn tube made of SUS316 was used for the test heat exchanger tube 411. A test heat exchanger shell 412 of the test heat exchanger 41 was made of a piping having an outside diameter of 34 mmφ and a thickness of 3.4 mm and provided with a spiral baffle in the inside thereof.

In addition, the circulating water of the cooling column for confirming a fouling removing effect was provided as a slurry W prepared by adding the precipitate recovered from the heat exchanger 21A in Example 1 to water in a concentration of 1,500 ppm. Then, the slurry W stored in a slurry tank 42 was fed to the side of the test heat exchanger tube 411 of the test heat exchanger 41 by a slurry circulation pump 43 and circulated into the slurry tank 42 via a reheater 44.

As a fouling evaluation method, an overall heat transfer coefficient U [U=Q/(A·Δt)] was determined using a quantity of heat Q [kcal/hr] determined from a temperature difference of a test cooling and heating medium H between a test cooling and heating medium inlet piping 401 and a test cooling and heating medium outlet piping 402 relative to the test heat exchanger 41, a logarithmic average temperature difference Δt [K] between a temperature of the slurry W and a temperature of the cooling and heating medium H, and a heat transfer area A [m$^2$] of the test heat exchanger 41.

In addition, the value of the overall heat transfer coefficient U is reduced by an increase of the heat transfer resistance due to fouling of the heat transfer surface with a lapse of time of cooling operation. Then, since a reciprocal of U rises with a lapse of time, an increment of the reciprocal of U from the beginning was designated as a fouling resistance Rf [hr·m$^2$·K/kcal]. Here, Rf is (1/U−1/U0), wherein U0 is U at the time when a fouling at the beginning of operation is not attached.

The quantity of heat Q [kcal/hr] was determined from Q=Wc·C·ΔTc using a flow rate Wc [kg/hr] of the cooling and heating medium H (warm water), a specific heat C [kcal/(kg·K)] of the cooling and heating medium H, and a temperature difference ΔTc [K] of the cooling and heating medium H between an outlet 402 and an inlet 401 relative to the test heat exchanger 41.

In addition, the logarithmic average temperature difference Δt [K] was determined from Δt=(Δt1−Δt2)/ln(Δt1/Δt2) using a temperature difference Δt1 of the cooling and heating medium H between a temperature of the inlet 401 and a temperature of a slurry outlet 422 and a temperature difference Δt2 of the cooling and heating medium H between a temperature of the outlet 402 and a temperature of a slurry inlet 421.

Figure 6:
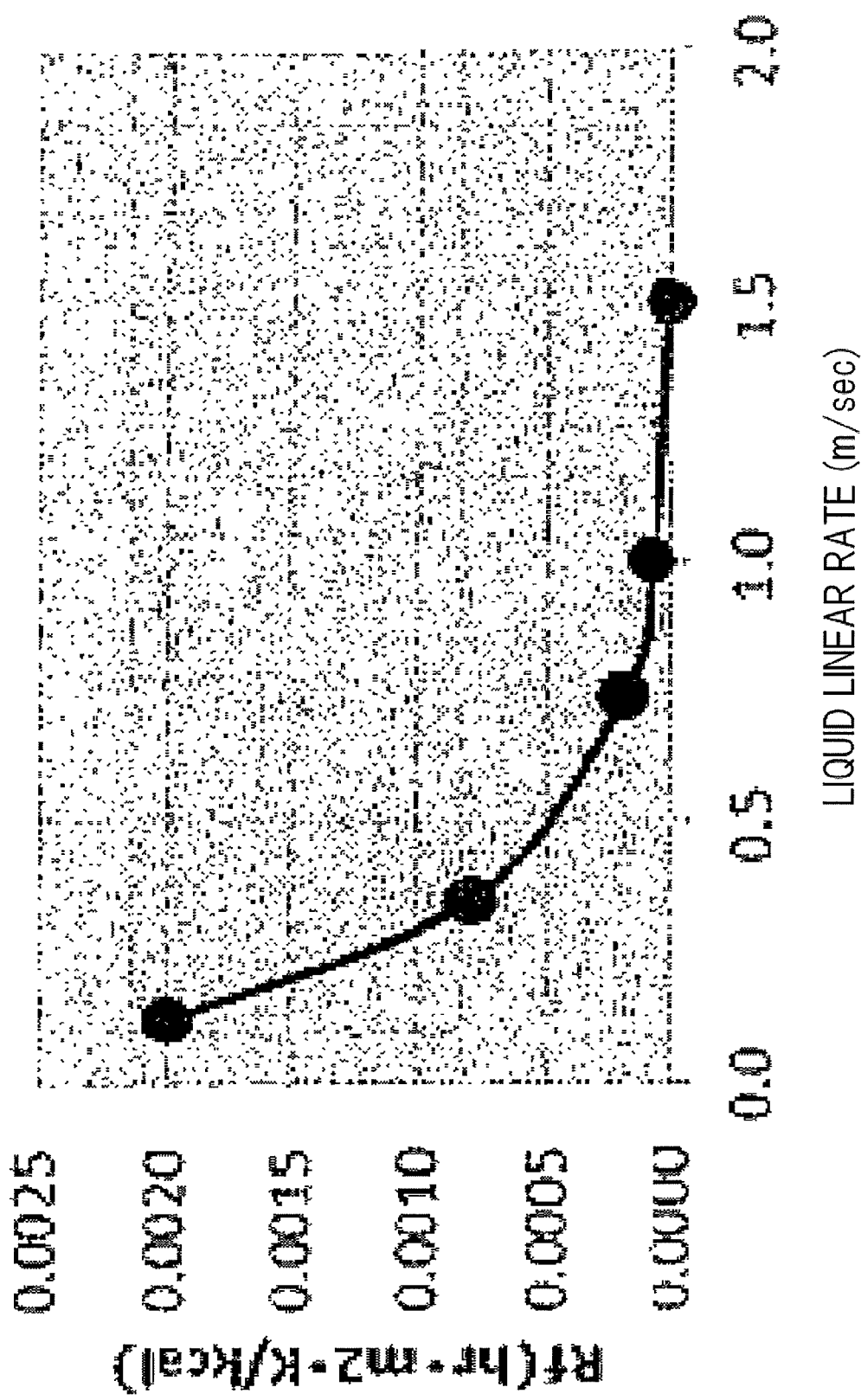
FIG. 6 is a graph showing a fouling resistance and a liquid linear velocity in a confirmation test.

Specific measurement conditions are shown in Table 3. In addition, a relation between the fouling resistance Rf and the liquid linear rate is shown in FIG. 6.

TABLE 3

| Experiment number | | | Reference Example 1 | Reference Example 2 | Reference Example 3 | Reference Example 4 | Reference Example 5 |
|---|---|---|---|---|---|---|---|
| Slurry W | Flow rate | kg/h | 37 | 113 | 236 | 319 | 478 |
| | Linear rate | m/sec | 0.12 | 0.35 | 0.74 | 1.0 | 1.5 |
| | Inlet temperature (401) | ° C. | 45 | 45 | 45 | 45 | 45 |
| | Outlet temperature (402) | ° C. | 37 | 41 | 42 | 42 | 43 |
| Cooling and heating medium H | Flow rate | kg/h | 77 | 76 | 76 | 76 | 76 |
| | Inlet temperature (421) | ° C. | 20 | 20 | 20 | 20 | 20 |
| | Outlet temperature (422) | ° C. | 24 | 26 | 28 | 32 | 33 |
| Rf (after 5 hours) | | hr · m$^2$ · K/kcal | 0.002 | 0.0008 | 0.0002 | 0.00008 | 0.00001 |

It is noted from Table 3 that the degree of attachment of the fouling component (Rf: fouling coefficient) varies with a difference of the liquid linear rate, and Reference Examples 1 to 3 are remarkably larger in the attachment than Reference Examples 4 to 5. The results reveal that as the liquid linear rate becomes larger, the fouling resistance Rf becomes smaller; and that in the method of precipitating the high boiling point by-product on the cooling transfer surface of the heat exchanger, it is preferred to regulate the liquid linear rate to 1.0 m/sec or less.

When the liquid linear rate is larger than 1.0 m/sec, the fouling resistance Rf becomes extremely small, so that it may be considered that the precipitated high boiling point by-product is exfoliated, or it passes through the heat exchanger without being precipitated. Namely, in the case where the liquid linear rate is more than 1.0 m/sec, and any measures are not taken, it is demonstrated that the high boiling point by-product is circulated into the cooling column and before long, is accumulated within the cooling column to become a concentration more than the solubility and precipitated in various spots to cause a factor that prevents the operation.

Comparative Example 1

The same operations as in Example 1 were followed, except that water at 25° C. was used as the cooling water of the heat exchangers 21A and 21B, to regulate the column top temperature of the cooling column 3 to 45° C. After elapsing 2 weeks, the one-stage discharge pressure and the two-stage discharge pressure of the compressor 4 were reduced to 0.3 MPaG and 0.1 MPaG respectively, and a pressure sufficient for introducing into the absorption column 5 was not obtained, so that the operation had to be stopped.

As a result of inspecting the compressor 4, it was found out that fouling was attached to suction and discharge valves. In addition, a large quantity of a yellow solid was also attached to the column top withdrawing piping 103 of the cooling column 3. As a result of analysis, it was noted that the yellow solid was a solid composed mainly of 9-fluorenone. The heat exchanger 21A was washed to recover a precipitate. However, the precipitate could not be quantitated because its amount was minute.

From the foregoing results, it was noted that in view of making the column top temperature of the cooling column 3 high, the 9-fluorenone transpired from the cooling column 3, and a necessity for cooling the circulating water by the heat exchanger to precipitate and remove the high boiling point by-product, such as 9-fluorenone, etc., was indicated.

Example 3

In a reaction tube inside the reactor 1 equipped with 113 reaction tubes each having an inner diameter of 27 mm and a length of 3,500 mm, 309 mL of the composite oxide catalyst produced in Production Example 1 and 398 mL of an inert ball (manufactured by Tipton Corp.) were packed per reaction tube. At this time, the catalytic layer was configured of three layers, and dilution ratios of the respective layers in the direction from the reactor inlet toward the product gas outlet of the reactor were 80% by volume, 60% by volume, and 25% by volume, respectively.

A raw material gas having a component composition shown in the foregoing Table 1, which was discharged from the extraction separation process of butadiene from the C4 fraction formed as a by-product in naphtha cracking, air, nitrogen, and steam were supplied into a preheater in flow rates of 15.9 $Nm^3/h$, 87.5 $Nm^3/h$, 55.9 $Nm^3/h$, and 17.7 $Nm^3/h$, respectively and heated at 217° C., and then supplied into a multitubular reactor from a raw material gas inlet.

A coolant at a temperature of 380° C. was flown into the body side of the reactor, thereby regulating a maximum temperature of the inside of the reaction tube to 412 to 415° C. The product gas withdrawn from the reactor was supplied into the cooling column, and the composition of the product gas was measured in the outlet of the cooling column and found as shown in the foregoing Table 2.

The cooling column is a 30-stage sieve tray column having an inside diameter of 304 mm as shown in FIG. 4, and the chimney is installed between the 20th stage and the 21st stage from above.

An effluent gas from the column top of the cooling column was subjected to pressure rising to 0.35 MPaG by the two-stage type reciprocating compressor 4 and introduced into the absorption column 5. A part of an effluent from the column bottom of the cooling column was circulated into the water spray apparatus 23 at a rate of 1,000 kg/h. Furthermore, the effluent was circulated into the lower part of the chimney at a rate of 1,000 kg/h.

An effluent water from the chimney was sent to the heat exchanger 21 at a rate of 1,500 kg/h. The heat exchanger 21 was configured of 2 tubes each having an outside diameter of 19 mm, a thickness of 1.65 mm, and a length of 4 m, circulating water was flown into the tubes, and cooling water at 5° C. was flown into the outside (body side) of the tubes. An inlet temperature of the circulating water of the heat exchanger 21 was 50° C., and an outlet temperature was regulated to 25° C. by an amount of the cooling water. A liquid linear rate within the tube was 1.08 m/sec.

The precipitate-containing circulating water having been cooled by the heat exchanger was sent to the separation apparatus 24A. The separation apparatus 24A was a 200-mesh SUS-made screen built-in strainer. In order to confirm the amount of the high boiling point by-product containing 9-fluorenone, etc. as accumulated in the separation apparatus 24A, the separation apparatus 24A was switched to the separation apparatus 24B having the same specification, and the operation was continued. During this, the separation apparatus 24A was left open, and the precipitate accumulated within the strainer was cleaned up with a brush. Since then, a switching operation between the separation apparatuses 24A and 24B at an interval of about one week for 2 months was performed.

During this, a concentration of 9-fluorenone in the circulating water was 17 ppm by weight, and the column top temperature of the cooling column remained constant at 25° C. In addition, a one-stage discharge pressure and a two-stage discharge pressure of the compressor 4 remained stable at 0.15 MPaG and 0.35 MPaG, respectively. In addition, the weight of the precipitate recovered by cleaning of the separation apparatuses 24A and 24B was 218 g per week in average.

Reference Example 6

To the circulating water 111 withdrawn from the chimney 22 shown in FIG. 4, the high boiling point by-product containing 9-fluorenone, etc. as recovered from the separation apparatus 24A was added in a concentration of 100 ppm to prepare a slurry liquid. About 50 mL of this slurry liquid was charged in a centrifugal filter (Model: SYK-3800, manufactured by Sanyo Rikagaku Co., Ltd., installed with a filter paper (Product Number: No. 4A, manufactured by Advantec) and centrifuged with setting a rotation speed adjustment scale (adjustable from 0 to 5, maximum rotation speed: 4,500 rpm) to 2. A filtrate which had flown out from this centrifugal filter was recovered and analyzed. As a result, the concentration of 9-fluorenone was 19 ppm by weight, so that it was demonstrated that a high boiling point product separation apparatus could be used as the centrifugal filter.

[Reference Examples 7 to 11] (Confirmation Test of Precipitation of High Boiling Point By-Product)

The same procedures as in Reference Examples 1 to 5 were followed, except that the precipitate recovered by the heat exchanger 21 in Example 3 was added to water in a concentration of 1,500 ppm to provide the slurry W.

Figure 7:
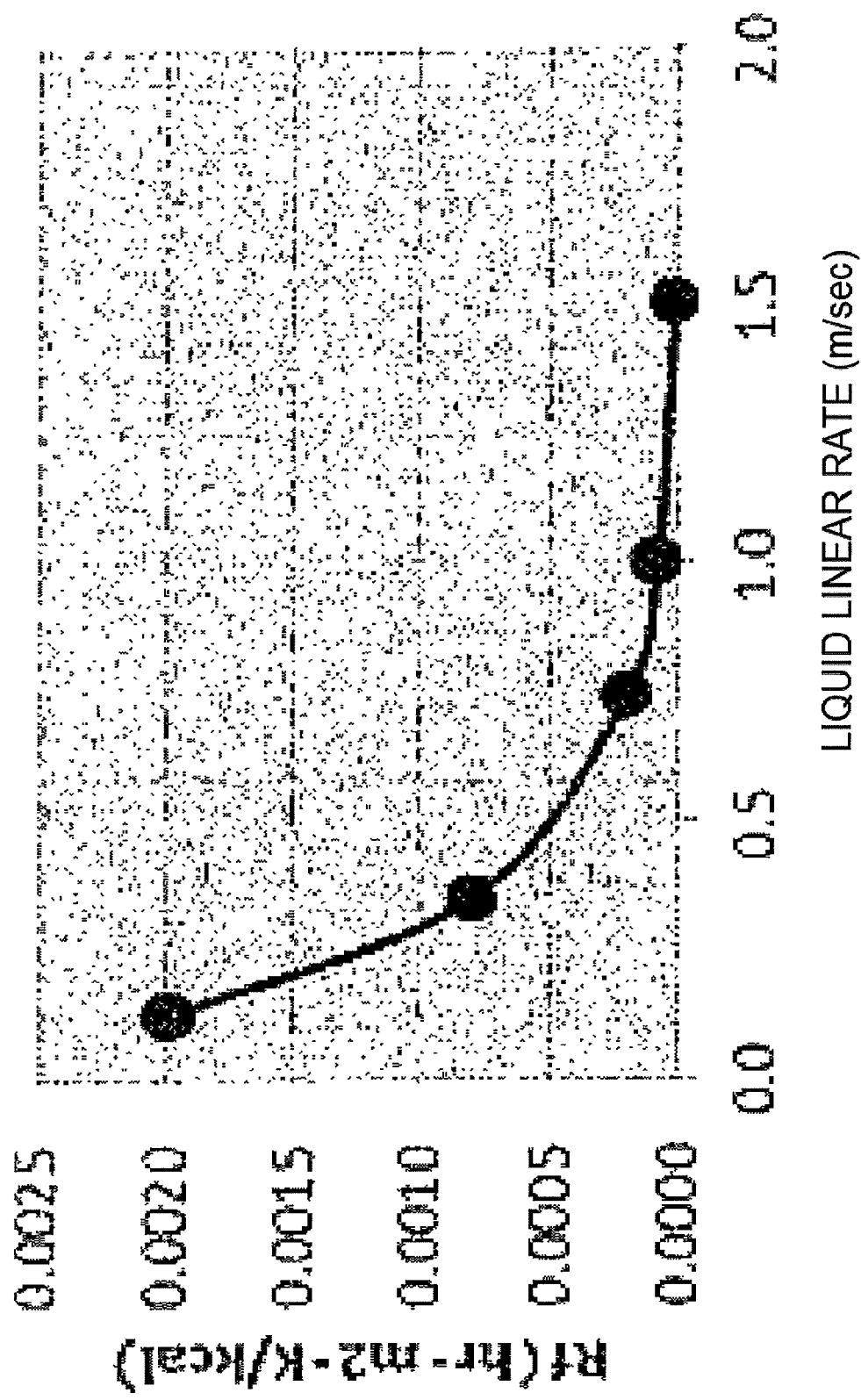
FIG. 7 is a graph showing a fouling resistance and a liquid linear velocity in a confirmation test.

Specific measurement conditions are shown in Table 4, and a relation between the fouling resistance Rf and the liquid linear rate is shown in FIG. 7.

TABLE 4

|  |  |  | Reference Example 7 | Reference Example 8 | Reference Example 9 | Reference Example 10 | Reference Example 11 |
|---|---|---|---|---|---|---|---|
| Slurry W | Flow rate | kg/h | 37 | 113 | 236 | 319 | 478 |
|  | Linear rate | m/sec | 0.12 | 0.35 | 0.74 | 1.0 | 1.5 |
|  | Inlet temperature (401) | °C. | 45 | 45 | 45 | 45 | 45 |
|  | Outlet temperature (402) | °C. | 37 | 41 | 42 | 42 | 43 |
| Cooling and heating medium H | Flow rate | kg/h | 77 | 76 | 76 | 76 | 76 |
|  | Inlet temperature (421) | °C. | 20 | 20 | 20 | 20 | 20 |
|  | Outlet temperature (422) | °C. | 24 | 26 | 28 | 32 | 33 |
| Rf (after 5 hours) |  | hr·m²·K/kcal | 0.002 | 0.0008 | 0.0002 | 0.00008 | 0.00001 |

From the foregoing results, it was confirmed that as the liquid linear rate becomes larger, the fouling resistance Rf becomes extremely smaller; and that when the liquid linear rate is made faster than 1.0 m/sec, the high boiling point by-product precipitated on the cooling transfer surface of the heat exchanger becomes extremely small.

Comparative Example 2

The same operations as in Example 3 were followed, except that the circulating water which had come out from the heat exchanger 21 was returned directly into the cooling column without using the separation apparatuses 24A and 24B. From right after beginning of the operation, a degree of opening of a control valve (not shown) for controlling a flow rate of the circulating water to be flown out from the chimney and circulated into the cooling column via the heat exchanger to 1,500 kg/h became gradually large, and the degree of opening of the control valve (not shown) became fully opened.

After elapsing 2 weeks after start of the operation, the flow rate of the circulating water at 1,500 kg/h could not be kept. Therefore, the operation was stopped, and the piping from the outlet of the heat exchanger 21 to the inlet of the cooling column 3 was left open. As a result, the attachment of a precipitate on the inner wall face of the piping was perceived and in particular, dominantly observed in a bent portion (elbow portion) of the piping. A recovery amount of the precipitate in the piping portion was 263 g, and a recovery amount of the precipitate within the cooling column was 155 g.

Comparative Example 3

The same operations as in Example 2 were followed, except that the heat exchanger 31B was configured of a tube having an outside diameter of 4 mm, a thickness of 1 mm, and a length of 5.7 m, and the liquid linear rate within the tube was changed to 1.06 m/sec. After operating the heat exchangers 31A and 31B for 144 hours, the heat exchanger 31B was left open, and a precipitate attached within the tube was cleaned up with a brush. Although 9-Fluorenone was not precipitated in the heat exchanger 31B, 9-fluorenone was precipitated in the piping 303.

While the invention has been described in detail and with reference to specific embodiments thereof, it will be apparent to one skilled in the art that various changes and modifications can be made therein without departing from the spirit and scope thereof. It is to be noted that the present application is based on a Japanese patent application filed on Mar. 9, 2015 (Japanese Patent Application No. 2015-046057) and a Japanese patent application filed on Mar. 19, 2015 (Japanese Patent Application No. 2015-056589), the entireties of which are incorporated by reference. In addition, all references cited herein are incorporated as a whole.

REFERENCE SIGNS LIST

1: Reactor
2: Gas cooling heat exchanger
3: Cooling column
4: Compressor
5: Absorption column
6: Deaeration column
7: Solvent separation column
20A, 20B: Tray or packing layer
21, 21A, 21B: Heat exchanger
22, 22A: Chimney
23: Water spray apparatus
24A, 24B: Separation apparatus
30A, 30B: Tray or packing layer
31A, 31B: Heat exchanger (single tube)
32: Chimney (single tube)
41: Test heat exchanger
42: Slurry tank
43: Slurry circulation pump
44: Reheater
100 to 111, 302 to 310: Piping
401: Test cooling and heating medium inlet piping
402: Test cooling and heating medium outlet piping
411: Test heat exchanger tube
412: Test heat exchanger shell
421: Slurry inlet
422: Slurry outlet
W: Slurry piping

The invention claimed is:

1. A method for producing a conjugated diene, the method comprising:
    subjecting a raw material gas comprising a monoolefin having a carbon number of 4 or more to an oxidative dehydrogenation reaction with a gas comprising molecular oxygen in the presence of a catalyst to obtain a reaction product gas comprising a conjugated diene; and
    subjecting the reaction product gas to a cooling step;
    wherein, in the cooling step, a cooling agent is supplied into a cooling column and is brought into contact with the reaction product gas,
    the cooling agent discharged from the cooling column is then cooled by at least one heat exchanger, a precipitate dissolved in the cooling agent is precipitated within the at least one heat exchanger and recovered, and the cooling agent from which the precipitate has been recovered is circulated into the cooling column;

wherein the cooling agent is water;

wherein a liquid linear rate in the at least one heat exchanger for precipitating the precipitate is 1.0 m/sec or less;

wherein the cooling column comprises an upper zone and a lower zone which are separated by a chimney, and the upper zone and the lower zone each comprise at least one tray; and wherein, in the cooling column, the reaction product gas is introduced to the lower zone, a mixture comprising a portion of the reaction product gas and the cooling agent is discharged from a bottom of the upper zone above the chimney, the mixture is directed through the at least one heat exchanger to obtain a cooled mixture, and the cooled mixture from which the precipitate has been recovered is directed to a top of the upper zone of the cooling column.

2. The method for producing a conjugated diene according to claim 1, wherein the precipitate is 9-fluorenone.

3. The method for producing a conjugated diene according to claim 2, wherein a concentration of 9-fluorenone in the cooling agent to be circulated into the cooling column is 30 ppm by weight or less.

4. The method for producing a conjugated diene according to claim 1, wherein two or more of the at least one heat exchangers are provided.

5. The method for producing a conjugated diene according to claim 4, wherein the two or more heat exchangers are arranged in at least either a parallel direction or a series direction.

6. The method for producing a conjugated diene according to claim 1, wherein the raw material gas is a gas comprising:
   1-butene, cis-2-butene, or tans-2-butene, each of which is obtained by dimerization of ethylene, or a mixture thereof;
   a butene fraction which is produced through a dehydrogenation or oxidative dehydrogenation reaction of n-butane; or
   a gas comprising a hydrocarbon having a carbon atom number of 4, which is obtained by performing fluid catalytic cracking of a fuel oil fraction.

7. A method for producing a conjugated diene, the method comprising:
   subjecting a raw material gas comprising a monoolefin having a carbon atom number of 4 or more to an oxidative dehydrogenation with a gas comprising molecular oxygen in the presence of a catalyst to obtain a reaction product gas comprising a conjugated diene; and
   subjecting the reaction product gas to a cooling stop;
   wherein, in the cooling step, a cooling agent is supplied into a cooling column and is brought into contact with the reaction product gas,
   the cooling agent discharged from the cooling column is then cooled by a condenser,
   a precipitate precipitated by cooling is recovered by at least one separation apparatus, and
   the cooling agent from which the precipitate has been recovered is circulated into the cooling column;
   wherein the cooling agent is water;
   wherein the condenser is heat exchanger, and a liquid linear rate in the condenser is faster than 1.0 m/sec;
   wherein the cooling column comprises an upper zone and a lower zone which are separated by a chimney, and
   the upper zone and the lower zone each comprise at least one tray; and
   wherein, in the cooling column, the reaction product gas is introduced to the lower zone,
   a mixture comprising a portion of the reaction product gas and the cooling agent is discharged from a bottom of the upper zone above the chimney,
   the mixture is directed through the at least one separation apparatus to obtain a cooled mixture, and
   the cooled mixture from which the precipitate has been recovered is directed to a top of the upper zone of the cooling column.

8. The method for producing a conjugated diene according to claim 7, wherein the precipitate is 9-fluorenone.

9. The method for producing a conjugated diene according to claim 8, wherein a concentration of 9-fluorenone in the cooling agent to be circulated into the cooling column is 30 ppm by weight or less.

10. The method for producing a conjugated diene according to claim 7, wherein two or more of the at least one separation apparatus are provided.

11. The method for producing a conjugated diene according to claim 7, wherein the raw material gas is a gas comprising:
    1-butene, cis-2-butene, or tans-2-butene, each of which is obtained by dimerization of ethylene, or a mixture thereof;
    a butene fraction which is produced through a dehydrogenation or oxidative dehydrogenation reaction of n-butane; or
    a gas comprising containing a hydrocarbon having a carbon atom number of 4, which is obtained by performing fluid catalytic cracking of a fuel oil fraction.

12. A method for producing a conjugated diene the method comprising:
    subjecting a raw material gas comprising a monoolefin having a carbon atom number of 4 or more to an oxidative dehydrogenation reaction with a gas comprising molecular oxygen in the presence of a catalyst, to obtain a reaction product gas comprising a conjugated diene; and
    subjecting the reaction product gas to a cooling step;
    wherein water is used as a cooling agent;
    wherein, in the cooling step, the cooling agent is supplied into a cooling column and is brought into contact with the reaction product gas, and the cooling agent discharged from the cooling column is then cooled by at least one heat exchanger and circulated into the cooling column;
    wherein the cooling column comprises an upper zone and a lower zone which are separated by a chimney, and
    the upper zone and the lower zone each comprise at least one tray;
    wherein, in the cooling column, the reaction product as is Introduced to the lower zone,
    a mixture comprising a portion of the reaction product gas and the cooling agent is discharged from a bottom of the upper zone above the chimney,
    the mixture is directed through the at least one heat exchanger and through at least one separation apparatus to obtain a cooled mixture, and the cooled mixture from which the precipitate has been recovered is directed to a top of the upper zone of the cooling column; and by regulating a liquid linear rate of the cooling agent passing through the at least one heat exchanger to 1.0 m/sec or less, 9-fluorenone is accumulated within the at least one heat exchanger, and the 9-fluorenone is separated from the cooling agent, or by making a liquid linear rate of the cooling agent passing through the at least one heat exchanger faster than 1.0 m/sec to pass through the at least one heat exchanger, the 9-fluorenone is then separated from the cooling agent by the at least one separation apparatus.

13. The method for producing a conjugated diene according to claim 12, wherein a concentration of 9-fluorenone in the cooling agent to be circulated into the cooling column is 30 ppm by weight or less.

14. The method for producing a conjugated diene according to claim 12, wherein the raw material gas is a gas comprising:
- 1-butene, cis-2-butene, or tans-2-butene, each of which is obtained by dimerization of ethylene, or a mixture thereof;
- a butene fraction which is produced through a dehydrogenation or oxidative dehydrogenation reaction of n-butane; or
- a gas comprising a hydrocarbon having a carbon atom number of 4, which is obtained by performing fluid catalytic cracking of a fuel oil fraction.

* * * * *

UNITED STATES PATENT AND TRADEMARK OFFICE
CERTIFICATE OF CORRECTION

| | |
|---|---|
| PATENT NO. | : 10,370,309 B2 |
| APPLICATION NO. | : 15/699666 |
| DATED | : August 6, 2019 |
| INVENTOR(S) | : Hiroki Hinoishi et al. |

Page 1 of 1

It is certified that error appears in the above-identified patent and that said Letters Patent is hereby corrected as shown below:

On the Title Page

Item (73), the Assignee Information is incorrect. Item (73) should read:
-- (73) Assignee: Mitsubishi Chemical Corporation, Chiyoda-ku (JP) --

Signed and Sealed this
Twenty-first Day of April, 2020

Andrei Iancu
*Director of the United States Patent and Trademark Office*